(12) United States Patent
Hu

(10) Patent No.: US 12,283,365 B2
(45) Date of Patent: Apr. 22, 2025

(54) ANOMALY DETECTION IN MEDICAL IMAGING DATA

(71) Applicant: Genentech, Inc.

(72) Inventor: Fang-Yao Hu, San Mateo, CA (US)

(73) Assignee: Genentech, Inc., South San Francisco, CA (US)

( * ) Notice: Subject to any disclaimer, the term of this patent is extended or adjusted under 35 U.S.C. 154(b) by 369 days.

(21) Appl. No.: 17/695,786

(22) Filed: Mar. 15, 2022

(65) Prior Publication Data

US 2022/0301689 A1 Sep. 22, 2022

Related U.S. Application Data

(60) Provisional application No. 63/161,864, filed on Mar. 16, 2021.

(51) Int. Cl.
*G16H 30/20* (2018.01)
*G06N 20/00* (2019.01)

(52) U.S. Cl.
CPC ............. *G16H 30/20* (2018.01); *G06N 20/00* (2019.01)

(58) Field of Classification Search
CPC ........ G16H 30/40; G16H 30/20; G16H 15/00; G16H 50/20; G16H 50/70; G06N 20/00; G06N 3/084; G06N 3/082; G06N 3/088; G06N 3/0475; G06N 3/0455; G06N 3/094

See application file for complete search history.

(56) References Cited

U.S. PATENT DOCUMENTS

| 10,176,579 | B2 * | 1/2019 | Chukka | .................. | G06T 7/0014 |
| 11,069,062 | B2 * | 7/2021 | Gregson | ................ | G16H 50/20 |

* cited by examiner

*Primary Examiner* — Tuan H Nguyen

(74) *Attorney, Agent, or Firm* — MORRISON & FOERSTER LLP

(57) ABSTRACT

Particular embodiments provide a method for anomaly detection in images of tissue. An image processing system may receive an image of a tissue sample. A set of tiles may be generated from the image of the tissue sample. The set of tiles may be input into an anomaly detection model comprising a generator model comprising functional skip-connections and a Markovian discriminator model. The anomaly detection model may be trained to isolate a feature space of normal tissue samples. Anomaly scores may be computed for the set of tiles, and an assessment may be generated for the image of the tissue sample based on the anomaly scores for the set of tiles. The assessment may include a reconstructed heatmap of the image of the tissue sample, wherein colors of the heatmap are selected based on the anomaly scores.

20 Claims, 18 Drawing Sheets

(14 of 18 Drawing Sheet(s) Filed in Color)

ANOMALY DETECTION IN MEDICAL IMAGING DATA

PRIORITY

This application claims the benefit, under 35 U.S.C. § 119(e), of U.S. Provisional Patent Application No. 63/161,864, filed 16 Mar. 2021, which is incorporated herein by reference.

TECHNICAL FIELD

The present disclosure relates to a computing system and methods using machine-learning algorithms to detect anomalies in medical imaging data.

BACKGROUND

High-performance anomaly detection models are desired across many fields. The general task of anomaly detection may involve the detection of abnormal samples residing outside the distribution of normal samples. The imbalance of normal and abnormal training data may demand anomaly detection models to train exclusively on normal data, yet detect general, unseen abnormal data. In security x-rays, for example, there may be abundant normal data, yet it may be crucial to detect unseen anomalies. Similarly, industrial inspection may have more access to normal samples, but detecting any abnormality may be crucial for proper quality assurance.

In safety assessment of a therapeutic treatment, pathology provides an important end-point for evaluating toxicity. For example, it is particularly important to determine which slides show normal, healthy histology and which are abnormal. Traditionally, pathologists typically review slides manually under a microscope. However, manual review by pathologists is time-consuming, requires high levels of expertise, and can be subjective. Even the best pathologists miss things and many abnormalities require very high magnification, which can take even more time, since the area to be examined increases proportionally to the magnification ratio and results in slide images comprising billions of pixels. Therefore, there is a need to digitize slides and perform automated analysis on them. The approach of performing exhaustive label annotation on the slides is still subject to the problem that identifying anomalies is tedious and difficult, however, due to the fact that the vast majority of tissue is normal.

Toxicologic histopathology typically also exhibits a data imbalance, where the quantity of normal data outweighs the abnormal data. However, despite the lack of available samples, it may be the abnormal data that demands selective attention. The variance of the distribution of abnormal samples may further challenge the task. The complexity of histopathological data may be another complication. Typically, abnormal pathological samples may closely resemble normal samples, which makes it difficult for current state-of-the-art methods to properly differentiate the data.

To address the above issues, researchers have been using machine learning to detect anomalies, which involves the detection of abnormal samples classified outside the distribution of normal samples. Conventional approaches use supervised learning to detect anomalies by relying on images labeled as "normal" and "abnormal" for training. However, such an approach has some limitations, stemming from the fact that the number of images of known normal samples far exceeds the number of images of known abnormal samples available for use in training, although it is the abnormal data that demands selective attention. First, the variance of the distribution of abnormal samples may be far broader than the examples available for use in training, which may cause the trained model to be ineffective at detecting novel anomalies. Second, abnormal pathological samples may closely resemble normal samples, which makes it particularly difficult to identify novel abnormal samples (that were not present in the training images). Third, the training images may include rarely occurring anomalies, which may introduce noise. Fourth, the training images may not include novel anomalies, which may cause the learned model to be ineffective at detecting such anomalies.

SUMMARY OF PARTICULAR EMBODIMENTS

The embodiments disclosed herein build an anomaly detection model by training on medical images depicting normal tissue. The anomaly detection model may incorporate aspects of a Generative Adversarial Network (GAN) model and an autoencoder. An image processing system may receive an image of a tissue sample and generate a set of tiles from the image of the tissue sample. The set of tiles may be input into an anomaly detection model comprising a generator model comprising functional skip-connections and a Markovian discriminator model. The anomaly detection model may be trained to isolate a feature space of normal tissue samples. Anomaly scores may be computed for the set of tiles, and an assessment may be generated for the image of the tissue sample based on the anomaly scores for the set of tiles. The assessment may include a reconstructed heatmap of the image of the tissue sample, wherein colors of the heatmap are selected based on the anomaly scores.

In some embodiments, the model may be trained solely using tiles labeled as depicting normal tissue, wherein such tiles may have been extracted from medical images depicting normal and abnormal tissue. By focusing solely on learning to isolate the feature space of normal tissue, the resulting model may be able to distinguish between normal tissue and anomalies.

The set of tiles may be generated by segmenting the image of the tissue sample into tiles at multiple scales of the image, where each of the scales is represented as multiple color channels of input (e.g., in the RGB color space). The multiple scales of the image may be concatenated to generate a hyper-dimensional image containing multiple levels of information. The heatmap may be reconstructed based on concatenating the multiple scales of the image. The heatmap may be reconstructed by mapping each unique score of the anomaly scores to a distinct color and generating the heatmap based on the mapping and the anomaly scores for the tiles.

The anomaly scores for each of the tiles may be computed as a function of a loss of the generator model and a loss of the discriminator model. The loss of the generator model may be determined as between the tile and a corresponding reconstruction of the tile. The loss of the discriminator model may be determined as between an output of the discriminator model for the tile and an output of the discriminator model for the corresponding reconstruction of the tile. The anomaly scores may be normalized to fall within a range from 0 to 1. Anomaly scores may be computed for each of a plurality of overlapping patches of the tiles.

Training the anomaly detection model may be designed to isolate a feature space of normal tissue samples. The model may be trained using a one-class data set comprising images of normal tissue. The anomaly detection model may involve jointly training the generator model and the discriminator model based on a combined loss comprising an adversarial loss, a reconstruction loss, and a latent loss. The adversarial loss may be a GAN loss that optimizes the model for precise reconstruction of normal histology images. The reconstruction loss may account for contextual information for local image regions by using a perceptual loss based on a structural similarity metric. The latent loss may optimizes the generator and discriminator to simultaneously learn the underlying distribution of normal data.

As an example and not by way of limitation, anomalies appearing in tissue samples may include indications of hypertrophy (hepatocyte hypertrophy, Kupffer cell hypertrophy, etc.), Kupffer cells (Kupffer cell pigmentation or Kupffer cell hypertrophy), or glycogen (glycogen depletion, etc.). As another example and not by way of limitation, the anomalies may be artifacts such as tissue folding, bubbles or dust, pen marker, etc.

In some embodiments, contextual information may be provided in the form of an additional image with a wider field of view. Besides tile-level anomaly detection, the architecture used for training the model can be also used for slide-level anomaly detection. Specifically, a first model based on the architecture is used on normal slides to generate normal heatmaps. A second model based on the same architecture takes the normal heatmaps as input and further predicts the slide-level anomaly scores.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DESCRIPTION

Recently, deep learning has advanced the field of anomaly detection, notably through the application of Generative Adversarial Networks (GANs) and autoencoders. These methods have demonstrated a promising ability to distinguish normal and abnormal data, but they require a simplification of the problem statement without accounting for the semantics of the anomaly detection problem. For example, current state-of-the-art methods are developed for artificial problems such as singling a class in CIFAR10 as abnormal, or using abnormal samples for a distribution with low variance for evaluation. These methods provide a good starting point, but performance may rapidly degrade when applying these methods to realistically complex tasks. The embodiments disclosed herein adopt a similar architecture and adds perceptual components, regularization techniques, and architectural changes that may improve performance.

A GAN architecture pairs a generative model with a discriminative model in order to learn a loss function on reconstructed images by generating plausible fake images and comparing them to real, in-distribution images. The generative model may be implemented using an autoencoder, which may learn to encode an unlabeled input image to a compressed latent space and then decode the representation from latent space back to an image. A variation (Skip-GANomaly) builds on traditional autoencoders by adding UNet-style skip-connections between layers of the generative model to thoroughly capture the multi-scale distribution of the normal data distribution in high-dimensional image space.

In embodiments disclosed herein, an anomaly detection model may be trained using solely images of normal tissue, and then subsequently be validated or deployed at an inference stage using images of both normal and abnormal tissue. The anomaly detection model may use a UNet-based generator network incorporating functional skip-connections that have been regularized to enhance model interpretability of normal data distributions. The anomaly detection model may use a Markovian discriminator (e.g., PatchGAN) to improve perceptual detection of localized anomalies. The anomaly detection model may use a perceptual loss that accounts for local interdependencies in complex images. The GAN-based architecture may leverage multi-scale information in anomaly detection to enhance regional interpretation of anomalies. Although this disclosure describes detecting particular anomalies via particular systems in particular manners, this disclosure contemplates detecting any suitable anomaly via any suitable system in any suitable manner.

Figure 1:
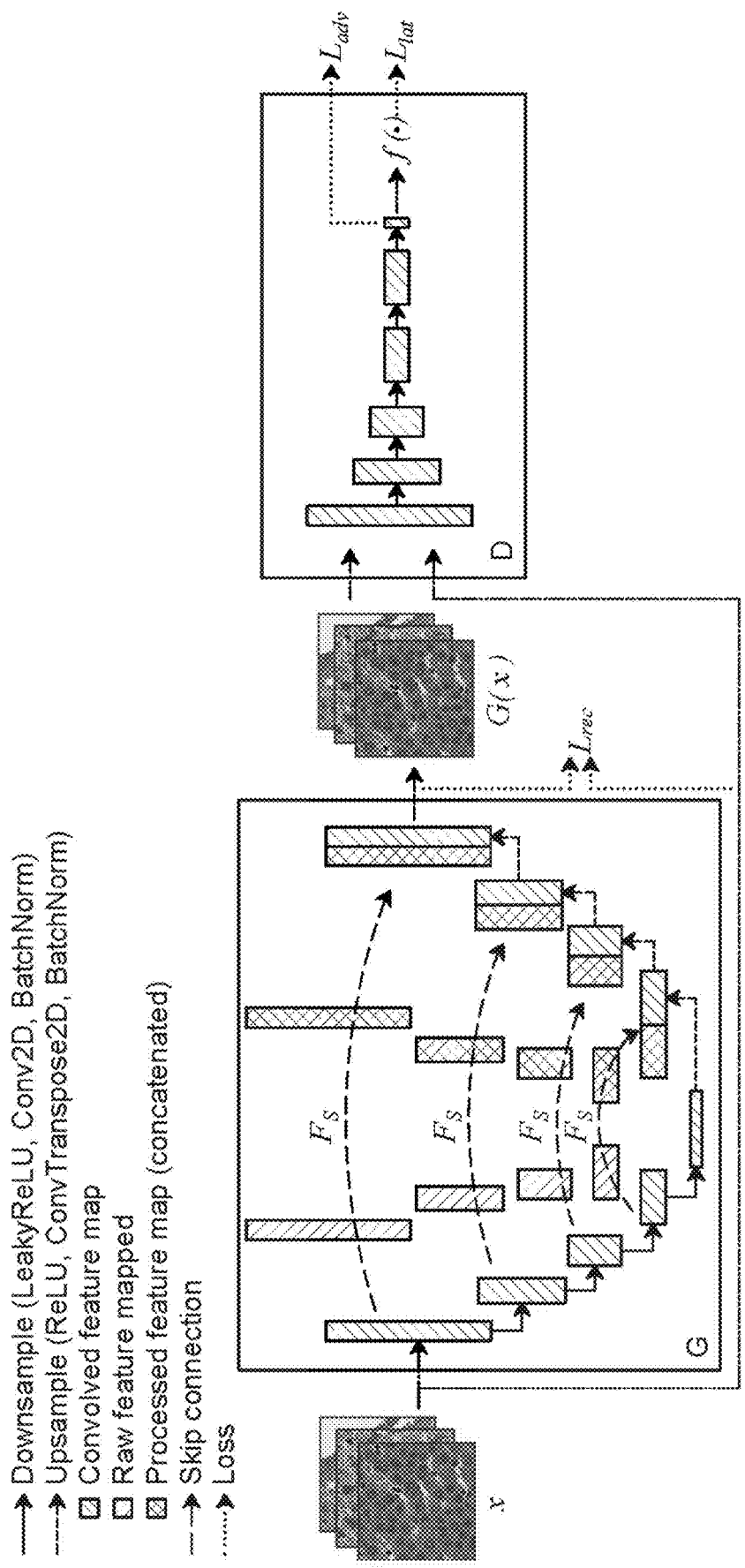
FIG. 1 illustrates an example anomaly detection model architecture.

FIG. 1 illustrates an example model architecture at the inference phase. The model architecture may comprise a UNet-based generator G with operable skip-connections Fs, and a discriminator D with its corresponding feature extractor f Each input image x (e.g., tiles of a whole slide image) is input into both the generative model G and the discriminative model D. Both the input image x and the output of the generative model G—reconstructed image G(x)—are input into the discriminative model D, which outputs the losses for both images.

In the training phase, a generator and discriminator are concurrently trained as per the traditional GAN framework. In addition to the adversarial training objective, custom objectives are designed to motivate anomaly detection. An anomaly score is derived from the outputs of both the generator and discriminator. As the model trains on normal data, the objectives drive the anomaly score for normal samples to a minimum. The model learns to isolate the feature space of normal data such that the generator understands the reconstruction parameters and discriminator understand differentiating parameters. Consequently, exposing the model to unseen, abnormal data should result in a simultaneous failure to reconstruct and discriminate, yielding a higher loss and therefore higher anomaly score. The ability for the model to separate the normal and abnormal anomaly score distributions measures its success. At the training phase, the loss for reconstructed image G(x) may be compared against the loss for the input image x and used to refine generative model G. This general architecture may be used for all models, with notable variations in Fs, D, $L_{rec}$, and the dimension of input image x.

The generator G may be based on the same encoder-decoder architecture as UNet. The layers of the generator network consist of symmetrical downsampling and upsampling convolutions. This architecture enables the model to learn the encoding of an input image into the latent feature space, as well as the decoding of latent vectors into the spatial dimension. The adversarial objective trains the model to output $G(x) \in R^{w \times h \times c}$ given the input image $x \in R^{w \times h \times c}$, such that the discriminator fails to distinguish between x and G(x). The anomaly detection objective reduces the spatial difference between x and G(x). The goal is to enhance the generator's understanding and ability to reconstruct normal data.

Significant architectural components of the generator are the skip-connections between the downsampling and upsampling layers. Traditionally, UNet employs skip-connections to assist with the reconstruction of high-frequency features. Leveraging skip-connections has proven to be a powerful technique that improves generator performance. Since skip-connections supply high-level information during image reconstruction, as well as provide alternative pathways during back-propagation, they support the generator's success regarding the adversarial objective. However, the generator's ability to accurately reconstruct images is detrimental towards the anomaly detection objectives if it is able to generalize to abnormal inputs. To address this issue, skip-connection processing (denoted as Fs) is introduced to enable to skip-connections to functionally support the anomaly detection objective.

A useful operation is applying Dropout to regularize the skip-connections and prevent the generator from overly depending on the skip-connections during reconstruction. Other possibilities include using autoencoders within the skip-connections to transform the connection from a direct concatenation of downsampling feature maps to a more contextual source of information. In general, employing functional skip-connections can greatly enable the generator towards the anomaly detection objective.

The discriminator D may be a convolutional neural network with the adversarial objective of distinguishing between real or generated images. In addition to the adversarial objective, the discriminator minimizes the difference between its real and fake features, $f(D(x))$ and $f(D(G(x)))$, which are typically vectors $z \in R^{n \times 1}$. The purpose is for the generator and discriminator to learn the underlying distribution of normal data. The large receptive field when using such an architecture results in instability. Embodiments disclosed herein utilize an alternative discriminator architecture based on PatchGAN that reduces the size of the receptive fields to small, overlapping patches. As a result, each localized patch receives a decision from the discriminator as opposed to a uniform decision for the input image. Instead of a latent vector, $z \in R^{n \times 1}$ where each element $z_{ij}$ refers to a 70 px by 70 px field of the original image. Anomaly detection performance improves because of the increase in perceptual precision, as the discriminator measures the per-patch normality of images.

Model training involves a combination of adversarial, reconstruction, and latent losses. The adversarial loss is a GAN loss that optimizes the model for precise reconstruction of normal histology images.

$$L_{adv} = _{x \sim p_x} E[\log D(x)] + _{x \sim p_x} E[\log(1 - D(G(x)))] \quad (1)$$

The reconstruction loss refines the generator performance in the spatial dimensions. Using a perceptual loss based on the structural similarity metric improves performance since it accounts for the contextual information of local image regions rather than per-pixel differences.

$$L_{rec} = E[L_{SSIM}(x, G(x))] \quad (2)$$

$$L_{SSIM}(x, y) = \left\| \frac{-(2\mu_x \mu_y + c_1)(2\sigma_{xy} + c_2)}{(\mu_x^2 + \mu_y^2 + c_1)(\sigma_x^2 + \sigma_y^2 + c2)} \right\| \quad (3)$$

The latent loss refines anomaly detection in the high-level latent dimensions. It optimizes the generator and discriminator to simultaneously learn the underlying distribution of normal data.

$$L_{lat} = _{x \sim p_x} E |f(D(x)) - f(D(G(x)))|_2 \quad (4)$$

The total loss is a weighted sum of the three losses, with $\lambda_{adv}=1$, $\lambda_{rec}=50$, and $\lambda_{lot}=1$.

$$L_{total} = \lambda_{adv} L_{adv} + \lambda_{rec} L_{rec} + \lambda_{lat} L_{lat} \quad (5)$$

The model was implemented in PyTorch and trained with a batch size of 128 on a NVIDIA V100 GPU. Both the generator and discriminator are trained on Adam optimizers with a learning rate of $10^{-4}$, $\beta_1=0.5$, and $\beta_2=0.999$. All models are trained for a minimum of 20 epochs and a maximum of 200 epochs with early stopping.

Figure 2:
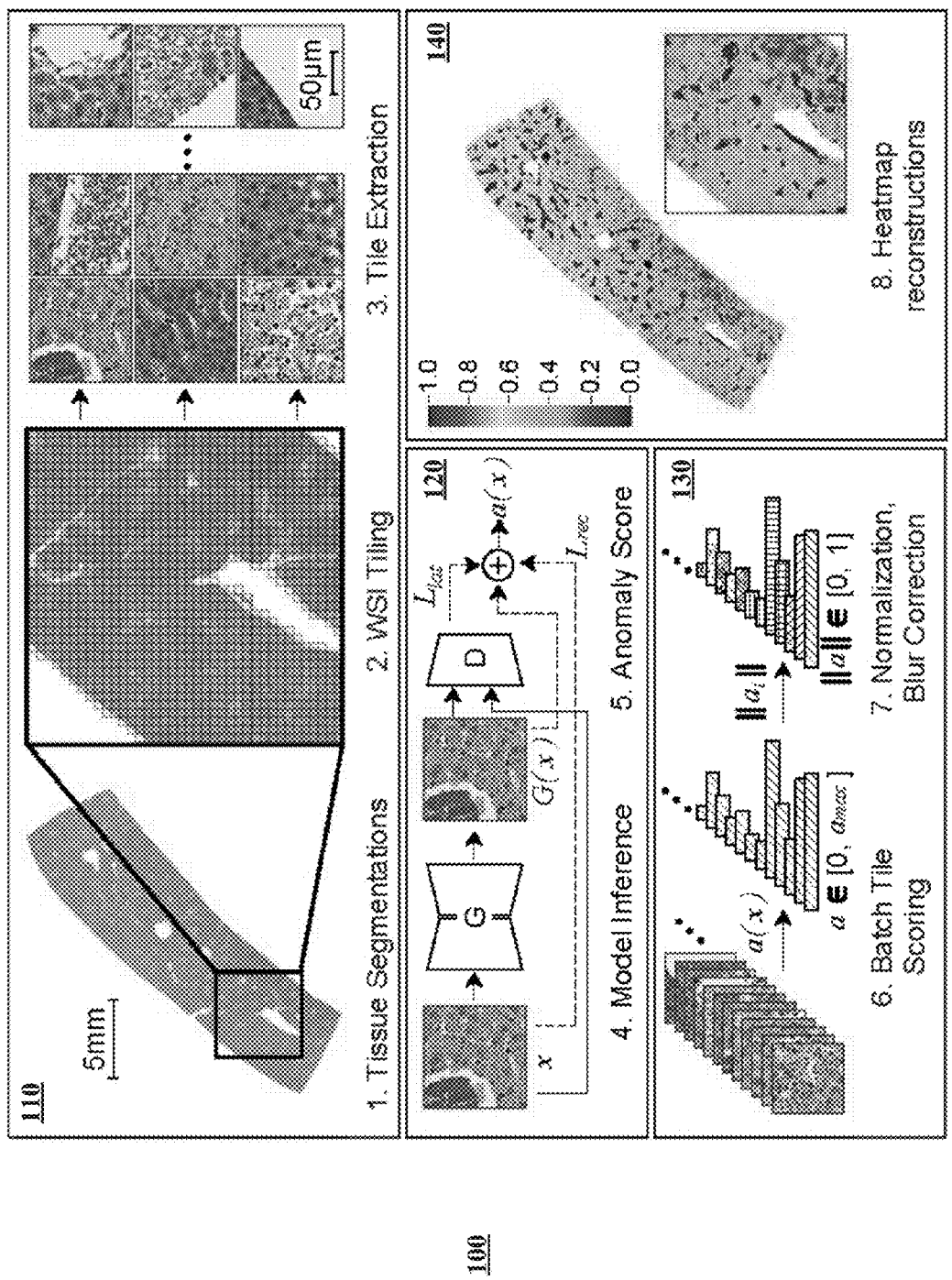
FIG. 2 illustrates an example workflow for anomaly detection for medical images.

FIG. 2 illustrates an example workflow 100 for unsupervised, single-class training of an anomaly detection model using images of normal tissue. At data pre-processing stage 110, images of tissue may be provided (e.g., as a whole-slide image, CAT scan image, MRI image). Each image of tissue may be tiled and tiles of interest extracted. A single WSI can measure over 100,000 px in one dimension and contain gigabytes of information. Current memory limitations demand the pre-processing of WSIs into tiles of a more manageable dimension. Consequently, the anomaly detection problem is reduced to anomaly detection on a per-tile basis. A shortcoming is the realistically inconsistent anomaly-to-tile ratio, combined with the depletion of different contexts of information. Abnormal regions can span over several tiles, and pathologists often inspect these regions at multiple magnifications to comprehensively understand the findings. Naively tiling a WSI neglects the spatial dependence between different tiles. Therefore, multi-scaling techniques are used to simultaneously incorporate high and low-level information, resulting in a more comprehensive model that detects anomalies using global and local contexts in multiple channels of input. Implementation requires the concatenation of multiple images of different scales that are symmetric about the same central pixel along the channel axis, resulting in a hyper-dimensional image containing multiple levels of information. In embodiments disclosed herein, 3-channel input was compared to 6-channel input.

At model inference stage 120, given an input image x, the generator G may reconstruct the image as G(x), and both the original input image x and the reconstructed image G(x) may be input into the discriminator D. The anomaly score may be a function of the loss between x and G(x), as well as the loss between discriminator output D(x) and D(G(x)). At post-processing stage 130, all original input images x may be scored in a batch process. The anomaly scores may be normalized, and other operations (e.g., blur correction) may be applied. At a heatmap reconstruction stage 140, the anomaly scores may processed into a reconstructed heatmap to visually depict anomalous histology findings.

The anomaly score may be derived as the weighted sum of the reconstruction and latent losses. The weighting parameter $w_{rec}$ controls the relative importance of the losses towards the final score. Embodiments disclosed herein may use $w_{rec}=0.9$ to apply more emphasis on the reconstruction loss.

$$a(x) = w_{rec} L_{rec} + (1 - w_{rec}) L_{lat} \qquad (6)$$

Since the generator and discriminator learn the distribution of normal data during training, it is expected that the anomaly scores for normal data are low at inference time. Conversely, a higher loss is indicative of poor image reconstruction, which implies that the input data is either unseen abnormal data or unseen normal data (with a higher likelihood of the former). Given the separation of normal and abnormal anomaly scores into lower and higher categories respectively, the area under the receiver operator characteristic curve (AUROC) is an effective performance metric. The AUROC metric provides a single scalar representing the ability of the model to properly segregate the abnormal and normal samples.

Practical usage of the anomaly scores also requires normalization to the range [0,1] which is performed as:

$$\hat{a}(x) = \frac{a(x) - \min(a)}{\max(a) - \min(a)} \qquad (7)$$

FIG. 2 summarizes an example pipeline of anomaly detection for toxicologic histopathology (TOXPATH), which encompasses data pre-processing, model inference, anomaly scoring, score normalization, and visualization. In practice, all tiles of individual slides feed into the model to obtain batches of anomaly scores. It is then possible to normalize the batch of scores of a slide for visualization. It is typical to have a control slide in TOXPATH studies, in which case normalization more appropriately occurs with respect to the control.

$$\hat{a}(x) = \frac{a(x) - \min(a_{control})}{\max(a_{control}) - \min(a_{control})} \qquad (8)$$

Experiments using embodiments described herein were conducted on an in-house TOXPATH dataset of normal histology and abnormal lesions from rat liver slides gathered from studies between 2012 and 2019. Study pathologists provided global diagnoses, and pathologists revisited these slides to generate pixel-level annotations. Thirteen of the slides were delegated as normal data, contributing 33,940 256 px by 256 px tiles. The remaining slides are split amongst the four abnormal classes and contribute to the validation dataset. Of interest are three types of lesions: necrosis (NEC), peritonitis (PER), and infiltrate (INF). Since many liver slides often also include a sample of spleen, spleen (SPL) is defined as a fourth anomaly class. In the experiments described herein, only normal data is used for training while NEC, PER, INF, and SPL are used for validation. There is variance between the abnormal classes, requiring generalization for high-performance. Additionally, some of the abnormal classes such as necrosis are similar to the normal data, requiring a high-degree of precision.

As seen in Table 1, most abnormal samples are of necrosis and spleen, with fewer of peritonitis and infiltrate. Acquiring data is challenging since infiltrates are small in size, while peritonitis occurs infrequently. The scarcity of abnormal data further demonstrates the value of training only on normal data. For each slide with abnormal findings, both normal and abnormal tiles are annotated and extracted to create balanced validation datasets.

TABLE 1

The in-house histopathology dataset was collected and reviewed with the help of expert pathologists.

|  | Slides | Normal Tiles | Abnormal Tiles |
|---|---|---|---|
| Normal | 13 | 33,940 | — |
| Necrosis (NEC) | 6 | 4,277 | 4,281 |
| Peritonitis (PER) | 11 | 470 | 70 |
| Infiltrate (INF) | 15 | 53 | 53 |
| Spleen (SPL) | 5 | 4,745 | 4,748 |
| Total | 50 | 43,287 | 9,552 |

In Table 1, 50 liver slides were annotated, with 13 normal slides delegated for training. The validation slides were chosen from abnormal finding in liver slides including necrosis, peritonitis, infiltrate, and presence of spleen. Abnormal slides contained a mixture of normal and abnormal tiles, which were selected to form balanced validation datasets.

An oversight in current anomaly detection studies is the omission of supervised out-of-distribution detection (ODD) results that motivate the usage of one-class classification. To that end, the experiment was conducted using a state-of-the-art supervised classifier on the in-house image dataset. Four classifiers were trained, each on a unique combination of the normal class training set and three of the four validation sets. For each model, one of the abnormal classes is dropped as the unseen class and the other classes are used for training. One slide from each class was held for validation. During validation, the model is exposed to data from all four classes to measure the ability of the model to not only classify seen classes, but correctly identify the examples not seen during training classes. Energy-based ODD is used to map samples to an energy based anomaly score yielding AUC scores which are analogous to the anomaly scores in the one-class classification approach.

$$A_{energy}(f, x) = -\log \sum_{i=0}^{nclasses} e^{f_i(x)} \qquad (9)$$

As shown in Table 2, accuracy may be low when classifying the seen classes using the traditional supervised approach. AUROC may also be low when exposing each supervised model to the respective unseen class. This finding reveals that it is difficult to obtain enough abnormal training data to excel at in-distribution classification, and it is also unfeasible for supervised approaches to identify unseen classes. This underlines the need for a one-class classification approach (as disclosed herein), in which a single-model is exposed to only normal training data, yet achieves high separability when simultaneously exposed to all unseen abnormal classes.

TABLE 2

Comparison between supervised multi-class
classification and embodiments disclosed
herein. Using a supervised approach on all but
one class results in high accuracy when
distinguishing the seen classes, but low AUROC
when exposed to the unseen class.

| Dropped Class | Supervised | | Ours (AUROC) |
|---|---|---|---|
| | In-distribution (Accuracy) | Out-of-distribution (AUROC) | |
| Necrosis | 0.708 | 0.477 | 0.897 |
| Peritonitis | 0.723 | 0.489 | 0.939 |
| Infiltrate | 0.77 | 0.496 | 0.994 |
| Spleen | 0.752 | 0.517 | 0.983 |

As indicated in Table 2, performance is much lower when the supervised models are exposed to the respective unseen class. This finding motivates the unsupervised approach that is only exposed to normal data when training, yet achieves high separability when exposed to all unseen abnormal classes.

Different alteration options (a higher dimensional input, Dropout on the skip-connections, perceptual SSIM loss as the reconstruction loss, and a PatchGAN discriminator) as applied to embodiments disclosed herein were evaluated in comparison against a baseline (Skip-GANomaly with 3-channel input based on the RGB color space) by evaluating each model's ability to separate the anomaly scores for normal and abnormal tiles using four different abnormal classes (necrosis, infiltrate, peritonitis, and spleen).

TABLE 3

Ablation studies: the baseline is shown in the first row.

| | Necrosis | Infiltrate | Peritonitis | Spleen | Average |
|---|---|---|---|---|---|
| SkipGANomaly (SG) – 3c | 0.730 | 0.923 | 0.985 | 0.970 | 0.902 |
| SkipGANomaly – 6c | 0.802 | 0.908 | 0.976 | 0.952 | 0.914 |
| SG + SkipDropout – 3c | 0.789 | 0.964 | 0.976 | 0.952 | 0.920 |
| SG + SSIM – 3c | 0.849 | 0.750 | 0.994 | 0.963 | 0.889 |
| SG + PatchGAN – 3c | 0.807 | 0.957 | 0.994 | 0.941 | 0.925 |
| SG + All – 3c | 0.928 | 0.983 | 0.988 | 0.957 | 0.964 |
| SG + All – 6c | 0.917 | 0.974 | 0.991 | 0.987 | 0.967 |

In Table 3, from the second to fifth rows inclusive, only one of the following alterations was added: 6-channel input—(RGB at the desired scale, plus RGB at a lower magnification scale), dropout on skip-connections, SSIM loss, and PatchGAN discriminator. The sixth row combines all additions except for the 6-channel input, and the last row contains all alterations. Dropout on the skip-connections and PatchGAN result in high individual contributions, while combining the various alterations yields the best overall performance.

Figure 3A:
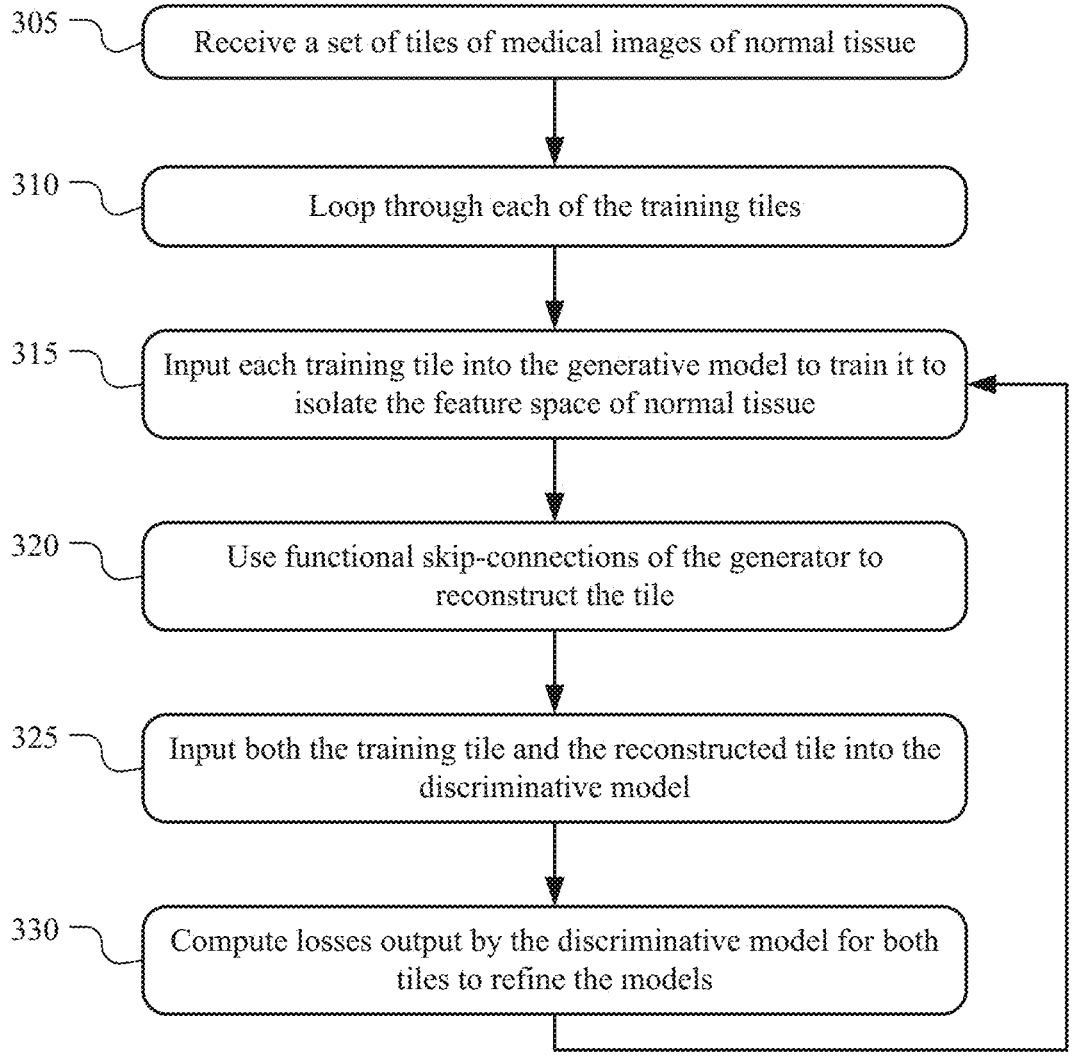
FIG. 3A is a flowchart of an example method for training an anomaly detection model to isolate the feature space of normal tissue in medical images.

FIG. 3A is a flowchart of an example method for training an anomaly detection model to isolate the feature space of normal tissue in medical images. At step 305, a set of training tiles depicting normal tissue (e.g., medical images) is received. At step 310, the method proceeds with the following steps for each of the training tiles. At step 315, the training tiles are input into the generative model to train it to isolate the feature space of normal tissue. At step 320, the generative model utilizes functional skip-connections to generate a reconstructed tile. As discussed above and in further detail below (particularly with respect to Table 4), modifying the skip-connections from their default behavior to operate in a functional and regularized manner can provide significant benefits, because it prevents the generative model from becoming overly dependent on the skip-connections. Since the objective is not reconstruction, but rather, anomaly detection, it is desirable to prevent the model from learning the specific features of abnormal tissue. At step 325, each of the training tile and the reconstructed tile are input into the discriminative model, and then at step 330, a loss (anomaly score) computed for the reconstructed tile is utilized to refine the generative model, and a loss (anomaly score) computed for the training tile is utilized to refine the discriminative model. By training the model based on a combination of adversarial loss, reconstruction loss, and latent loss, where the reconstruction loss uses a perceptual loss based on the structural similarity metric, the model is able to account for contextual information provided by local image regions (patches).

Figure 3B:
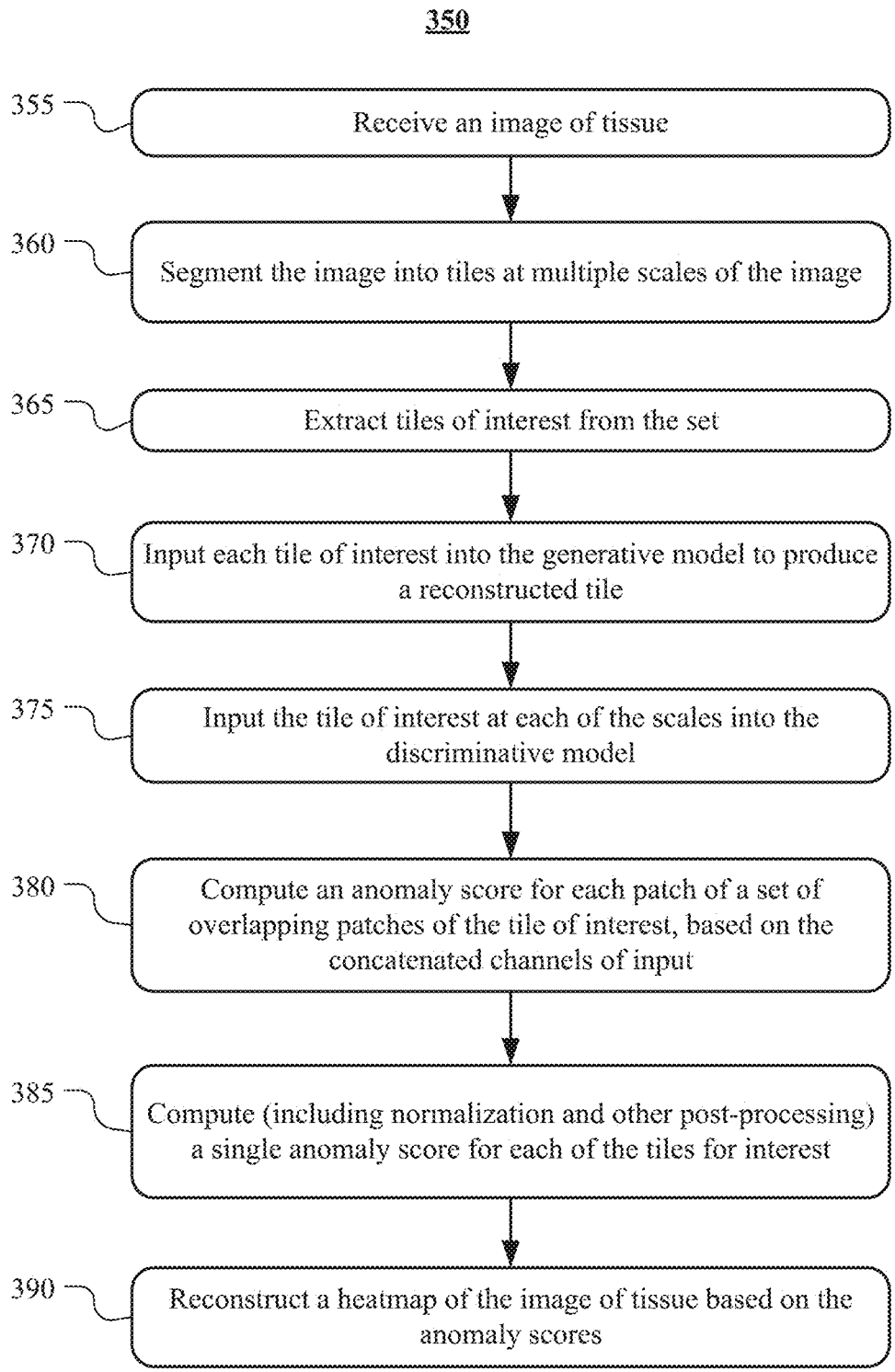
FIG. 3B is a flowchart of an example method for utilizing an anomaly detection model to identify anomalies in a medical image of tissue.
Figure 4A:
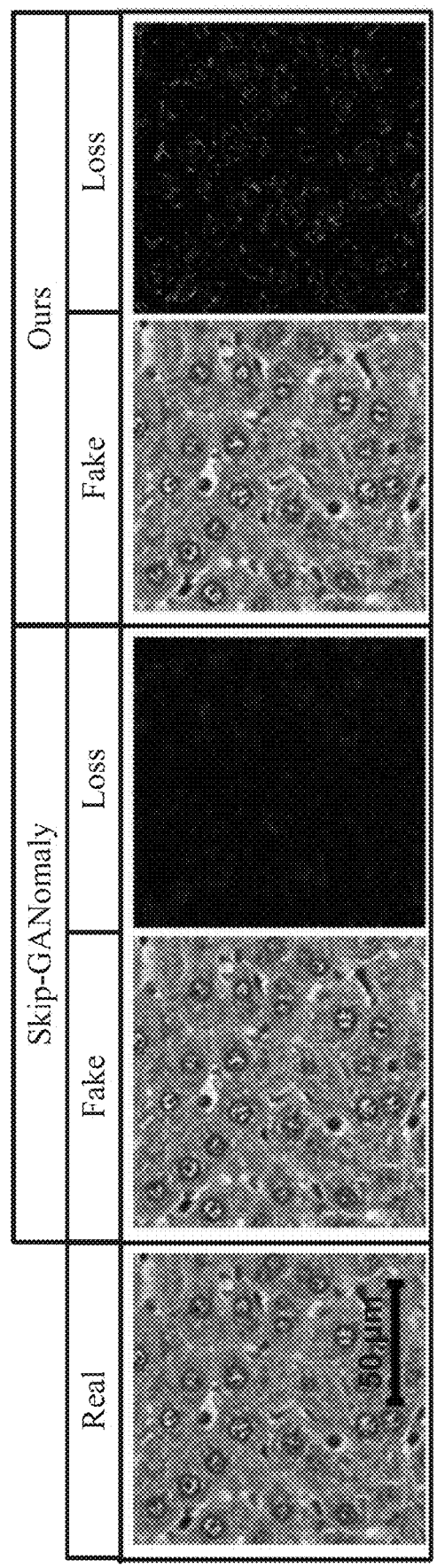
FIGS. 4A-4F illustrate example representative examples of reconstructions.
Figure 4B:
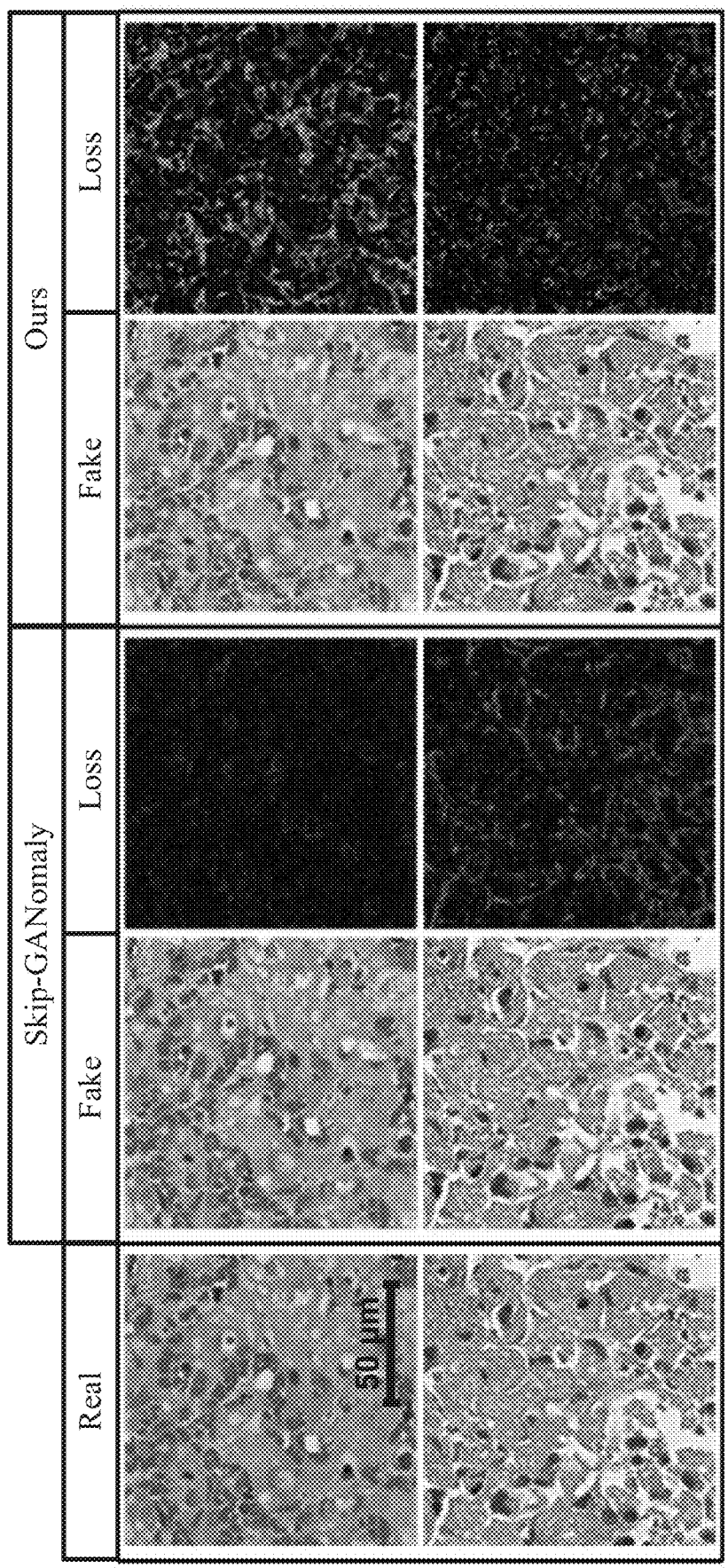
Figure 4C:
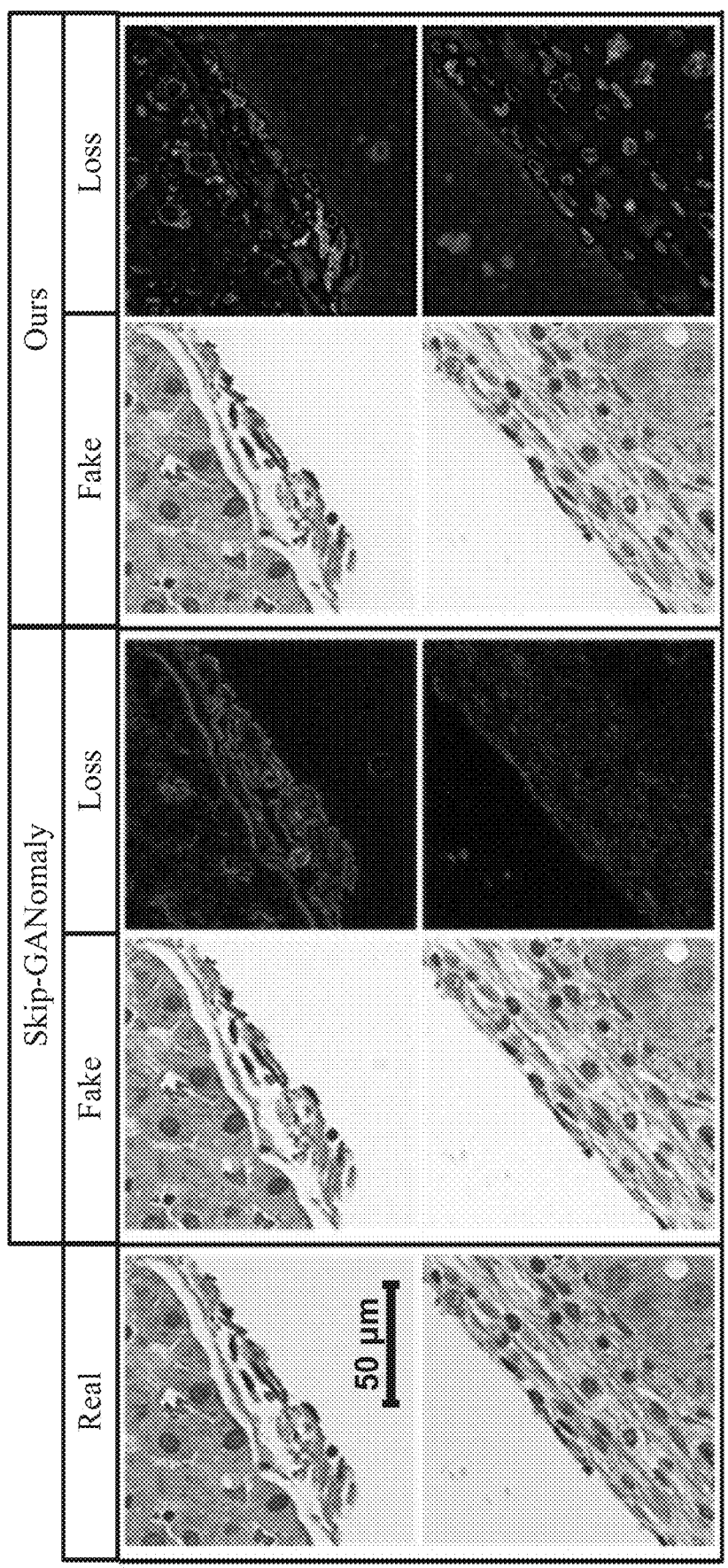
Figure 4D:
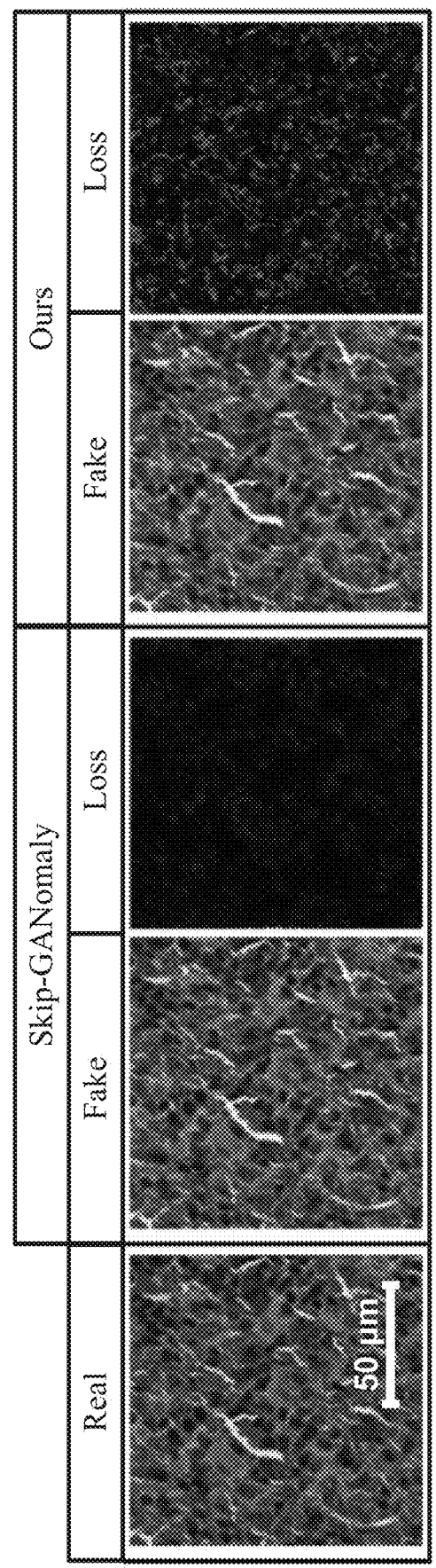
Figure 4E:
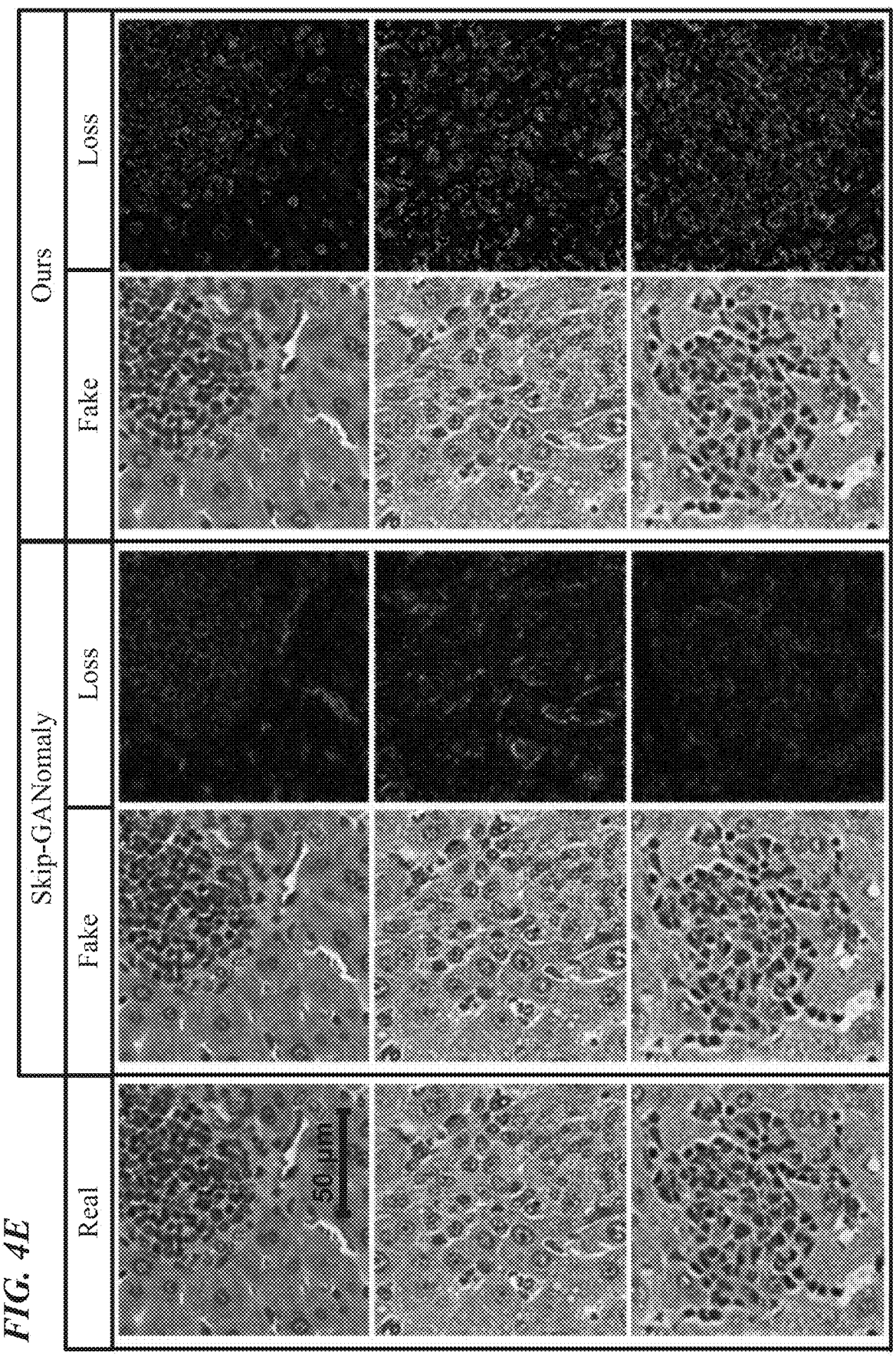
Figure 4F:
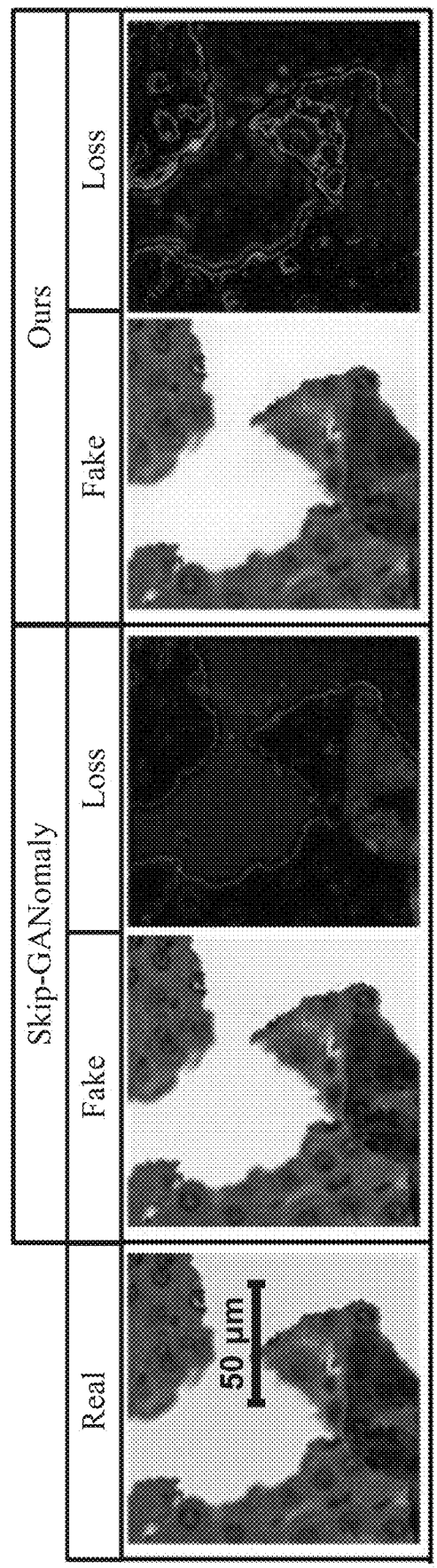
Figure 5A:
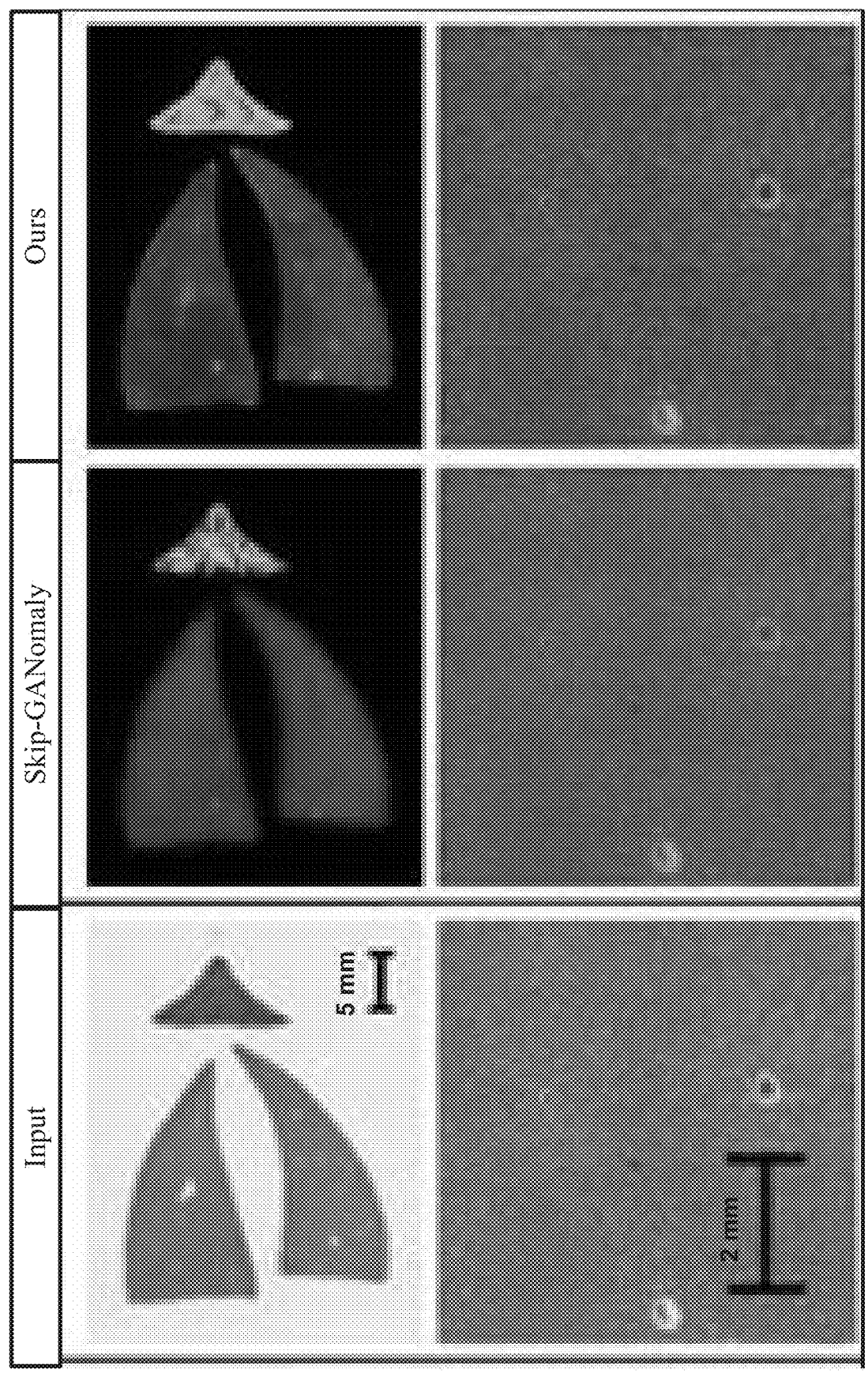
FIGS. 5A-5F illustrate example representative heatmaps and regions of interest.
Figure 5B:
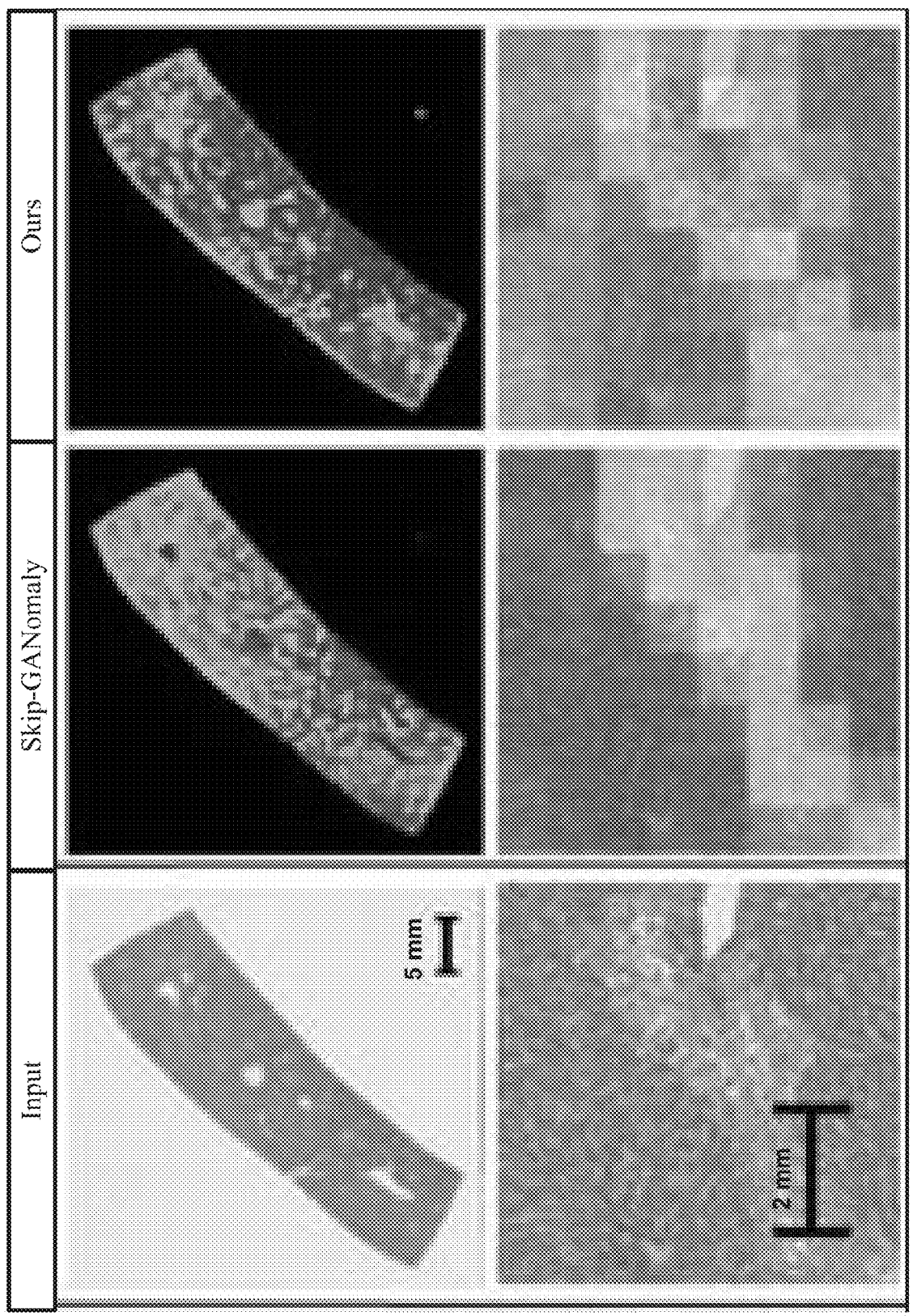
Figure 5C:
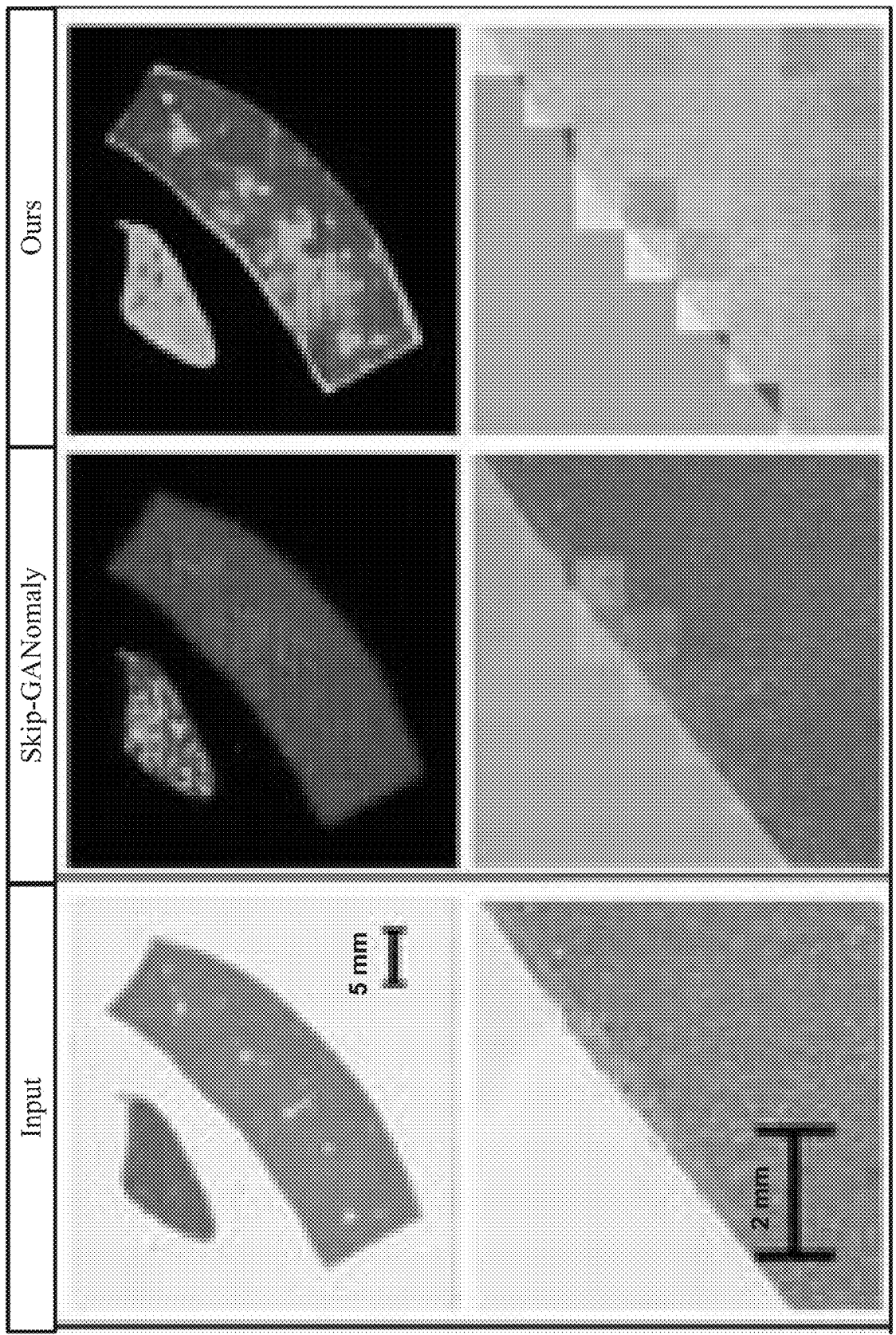
Figure 5D:
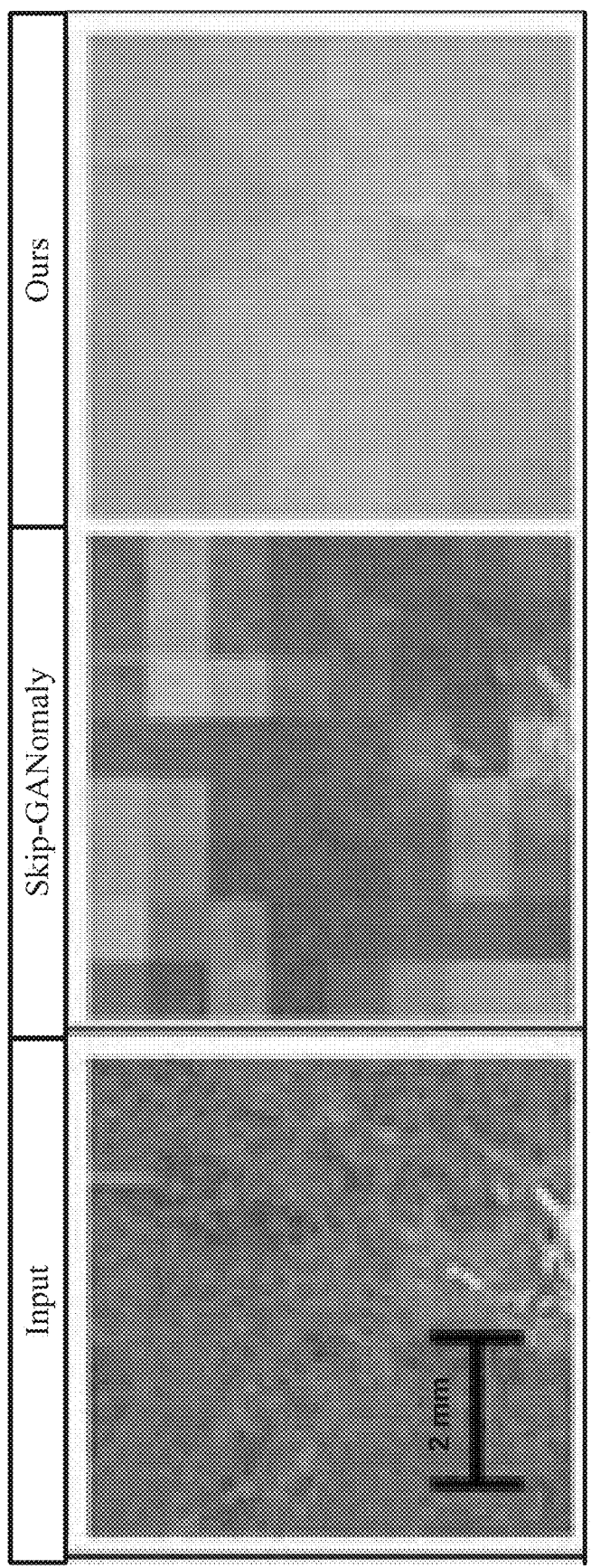
Figure 5E:
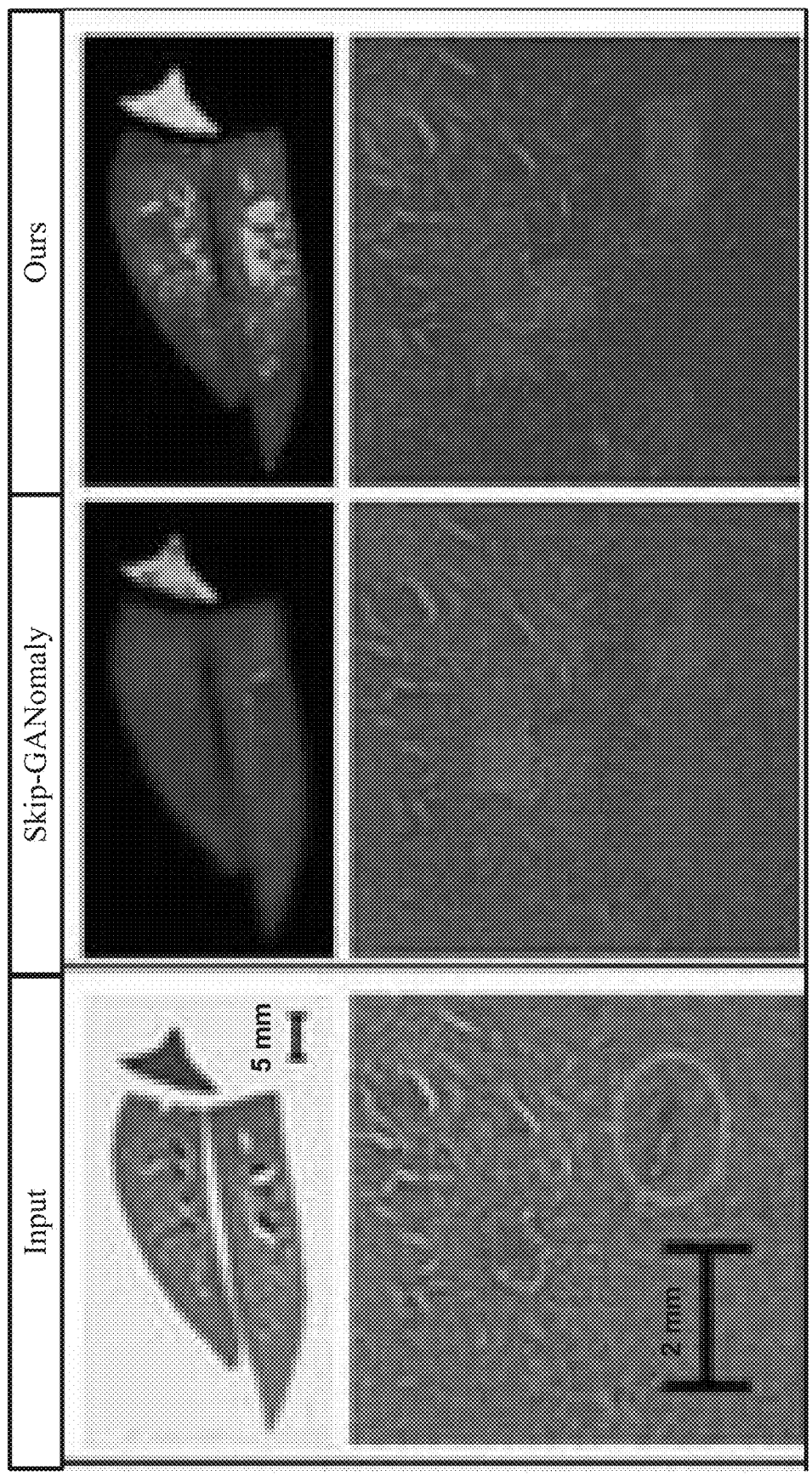
Figure 5F:

FIG. 3B is a flowchart of an example method for utilizing an anomaly detection model to identify anomalies in a medical image of tissue, as explained with respect to the workflow illustrated in FIG. 2. At step 355, an image of tissue is received. The image may be, by way of example and not limitation, a WSI, an MRI image, or a CAT scan image. At step 360, the image may be segmented into a tiles at multiple scales of magnification of the image (e.g., 6 channels of input at two scales of an image represented in the RGB color space). At step 365, tiles of interest may be extracted from the set. At step 370, each of the tiles of interest may be input into the generative model to produce a reconstructed version of the tile. At step 375, the tile of interest (at each of the multiple scales) may be input into the discriminative model. At step 380, an anomaly score may be computed for each patch of a set of overlapping patches of the tile of interest, based on the concatenated channels of input. The Markovian discriminator is able to improve perceptual detection of localized anomalies through measurement of per-patch normality. At step 385, a single anomaly score for each of the tiles is computed, including applying normalization and other post-processing steps. At step 390, a heatmap of the image of tissue is reconstructed, based on the anomaly scores for each tile, to provide a visualization of any identified anomalies in the tissue.

FIGS. 4A-4F illustrate example representative examples of reconstructions of tissue samples (from the input image shown in the "Real" column) and compare the results of the fake image reconstructed when using skip connections in the autoencoder (as with the Skip-GANomaly technique) to the results of the fake image when using functional skip connections in the autoencoder (as with embodiments described herein). FIGS. 4A-4F illustrate examples of reconstruction of patch(es) of different types of tissue, including a normal tissue image (FIG. 4A) and abnormal tissue images illustrating various anomalies in FIGS. 4B-4F (necrosis, peritonitis, spleen, infiltrate, and a tissue tear, respectively). As shown in FIGS. 4A-4F, embodiments disclosed herein result in a higher reconstruction loss for images including abnormal tissue, which indicates better detection of anomalies. Physical anomalies such as tears were not considered during evaluation, yet the model still detected them as abnormal which further demonstrates the ability of the embodiments disclosed herein to generalize to unseen abnormal classes. (Note: the scale bar in the real, normal tissue image in FIG. 4A measures 50 µm. FIGS. 4A-4F are all at the same scale.)

Further validation of embodiments on alternate image sets illustrates a meaningful improvement achieved by embodiments disclosed herein when measured against Skip-GANomaly as a baseline. Dropout provides regularization that may mitigate the over-dependence of reconstructions on the skip-connections, which optimizes the model for anomaly detection rather than naive reconstructions.

TABLE 4

Dropout on the skip-connections had a significant individual impact on histology data

|  | Baseline | Dropout on skip-connections |
|---|---|---|
| Bottle | 0.780 | 0.897 |
| Cable | 0.596 | 0.740 |
| Capsule | 0.695 | 0.741 |
| Carpet | 0.895 | 0.913 |
| Grid | 0.960 | 0.971 |
| Hazelnut | 0.934 | 0.999 |
| Leather | 0.972 | 0.994 |
| Metal Nut | 0.558 | 0.690 |
| Pill | 0.908 | 0.850 |
| Screw | 1.000 | 1.000 |
| Tile | 0.962 | 0.934 |
| Toothbrush | 0.846 | 0.879 |
| Transistor | 0.550 | 0.786 |
| Wood | 0.990 | 0.997 |
| Zipper | 0.752 | 0.898 |

As indicated in Table 4, use of the Dropout technique on the skip-connections also resulted in the most improvement (based on measured AUC) on standard industrial data from MVTec, outperforming the baseline Skip-GANomaly on 13 of the 15 classes.

FIGS. 5A-5F illustrate example representative heatmaps for regions of interest and compare the results of the normalized anomaly scores computed when using skip connections in the autoencoder (as with the Skip-GANomaly technique) to the results of the fake image when using functional skip connections in the autoencoder (as with embodiments described herein). FIGS. 5A-5F illustrate examples representative heatmaps for regions of interest of different types of tissue, including a normal tissue image (FIG. 5A) and abnormal tissue images illustrating various anomalies in FIGS. 5B-5F (necrosis, peritonitis, spleen, infiltrate, and a tissue tear, respectively). As shown in FIGS. 5A-5F, embodiments disclosed herein result in significantly higher contrast between normal and abnormal regions compared to Skip-GANomaly, particularly when highlighting regions of peritonitis, which generally manifest near the edges of livers. The baseline struggles to highlight the spleen, despite the contrast between the spleen and liver tissues. Infiltrate has been highlighted by a green circle (see FIG. 5E) to demonstrate the ability of embodiments disclosed herein to identify small lesions. (Note: scale bar in the whole slide image measures 5 mm. In the tiles, scale bar measures 2 mm.)

TABLE 5

Incorporating other skip-connection modifications.

|  | Baseline | Autoencoder on skip-connections |
|---|---|---|
| Bottle | 0.780 | 0.949 |
| Cable | 0.596 | 0.827 |
| Capsule | 0.695 | 0.742 |
| Carpet | 0.895 | 0.907 |
| Grid | 0.960 | 0.976 |
| Hazelnut | 0.934 | 0.956 |
| Leather | 0.972 | 0.968 |

TABLE 5-continued

Incorporating other skip-connection modifications.

|  | Baseline | Autoencoder on skip-connections |
|---|---|---|
| Metal Nut | 0.558 | 0.606 |
| Pill | 0.908 | 0.843 |
| Screw | 1.000 | 1.000 |
| Tile | 0.962 | 0.822 |
| Toothbrush | 0.846 | 0.929 |
| Transistor | 0.550 | 0.841 |
| Wood | 0.990 | 0.985 |
| Zipper | 0.752 | 0.754 |

As indicated in Table 5, incorporating other skip-connection modifications such as autoencoders on the skip-connections demonstrates promising results, outperforming the baseline Skip-GANomaly on 11 of the 15 classes from the industrial MVTec dataset. Changing the skip-connections has a significant impact anomaly detection performance, and is undergoing further study and experimentation.

Figure 6:
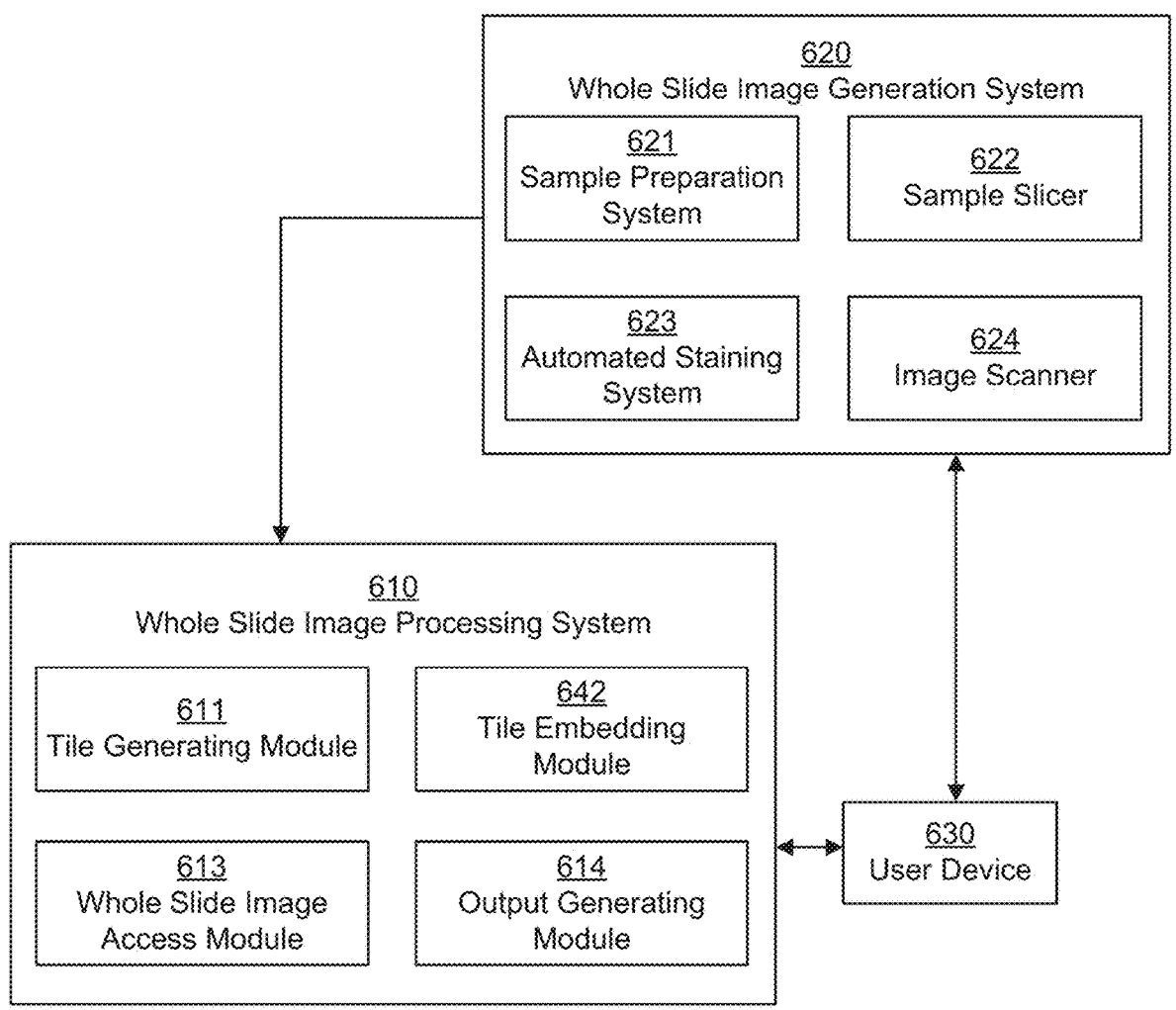
FIG. 6 illustrates an example network of interacting computer systems for generating whole slide images (WSI).

FIG. 6 illustrates an example network 600 of interacting computer systems for processing whole slide images (WSI) according to some embodiments of the present disclosure. A whole slide image generation system 620 can generate one or more whole slide images or other related digital pathology images, corresponding to a particular sample. For example, an image generated by whole slide image generation system 620 can include a stained section of a biopsy sample. As another example, an image generated by whole slide image generation system 620 can include a slide image (e.g., a blood film) of a liquid sample. As another example, an image generated by whole slide image generation system 620 can include fluorescence microscopy such as a slide image depicting fluorescence in situ hybridization (FISH) after a fluorescent probe has been bound to a target DNA or RNA sequence.

Some types of samples (e.g., biopsies, solid samples and/or samples including tissue) can be processed by a sample preparation system 621 to fix and/or embed the sample. Sample preparation system 621 can facilitate infiltrating the sample with a fixating agent (e.g., liquid fixing agent, such as a formaldehyde solution) and/or embedding substance (e.g., a histological wax). For example, a sample fixation sub-system can fix a sample by exposing the sample to a fixating agent for at least a threshold amount of time (e.g., at least 3 hours, at least 6 hours, or at least 63 hours). A dehydration sub-system can dehydrate the sample (e.g., by exposing the fixed sample and/or a portion of the fixed sample to one or more ethanol solutions) and potentially clear the dehydrated sample using a clearing intermediate agent (e.g., that includes ethanol and a histological wax). A sample embedding sub-system can infiltrate the sample (e.g., one or more times for corresponding predefined time periods) with a heated (e.g., and thus liquid) histological wax. The histological wax can include a paraffin wax and potentially one or more resins (e.g., styrene or polyethylene). The sample and wax can then be cooled, and the wax-infiltrated sample can then be blocked out.

A sample slicer 622 can receive the fixed and embedded sample and can produce a set of sections. Sample slicer 622 can expose the fixed and embedded sample to cool or cold temperatures. Sample slicer 622 can then cut the chilled sample (or a trimmed version thereof) to produce a set of sections. Each section can have a thickness that is (for example) less than 600 μm, less than 50 μm, less than 60 μm or less than 5 μm. Each section can have a thickness that is (for example) greater than 0.1 µm, greater than 6 µm, greater than 2 µm or greater than 4 µm. The cutting of the chilled sample can be performed in a warm water bath (e.g., at a temperature of at least 30° C., at least 35° C. or at least 40° C.).

An automated staining system 623 can facilitate staining one or more of the sample sections by exposing each section to one or more staining agents. Each section can be exposed to a predefined volume of staining agent for a predefined period of time. In some instances, a single section is concurrently or sequentially exposed to multiple staining agents.

Each of one or more stained sections can be presented to an image scanner 624, which can capture a digital image of the section. Image scanner 624 can include a microscope camera. The image scanner 624 can capture the digital image at multiple levels of magnification (e.g., using a 60× objective, 20× objective, 40× objective, etc.). Manipulation of the image can be used to capture a selected portion of the sample at the desired range of magnifications. Image scanner 624 can further capture annotations and/or morphometrics identified by a human operator. In some instances, a section is returned to automated staining system 623 after one or more images are captured, such that the section can be washed, exposed to one or more other stains, and imaged again. When multiple stains are used, the stains can be selected to have different color profiles, such that a first region of an image corresponding to a first section portion that absorbed a large amount of a first stain can be distinguished from a second region of the image (or a different image) corresponding to a second section portion that absorbed a large amount of a second stain.

It will be appreciated that one or more components of whole slide image generation system 620 can, in some instances, operate in connection with human operators. For example, human operators can move the sample across various sub-systems (e.g., of sample preparation system 621 or of whole slide image generation system 620) and/or initiate or terminate operation of one or more sub-systems, systems, or components of whole slide image generation system 620. As another example, part or all of one or more components of whole slide image generation system (e.g., one or more subsystems of the sample preparation system 621) can be partly or entirely replaced with actions of a human operator.

Further, it will be appreciated that, while various described and depicted functions and components of whole slide image generation system 620 pertain to processing of a solid and/or biopsy sample, other embodiments can relate to a liquid sample (e.g., a blood sample). For example, whole slide image generation system 620 can receive a liquid-sample (e.g., blood or urine) slide; that includes a base slide, smeared liquid sample and cover. Image scanner 624 can then capture an image of the sample slide. Further embodiments of the whole slide image generation system 620 can relate to capturing images of samples using advancing imaging techniques, such as FISH, described herein. For example, once a florescent probe has been introduced to a sample and allowed to bind to a target sequence appropriate imaging can be used to capture images of the sample for further analysis.

A given sample can be associated with one or more users (e.g., one or more physicians, laboratory technicians and/or medical providers) during processing and imaging. An associated user can include, by way of example and not of limitation, a person who ordered a test or biopsy that produced a sample being imaged, a person with permission to receive results of a test or biopsy, or a person who conducted analysis of the test or biopsy sample, among others. For example, a user can correspond to a physician, a pathologist, a clinician, or a subject. A user can use one or more user devices 630 to submit one or more requests (e.g., that identify a subject) that a sample be processed by whole slide image generation system 620 and that a resulting image be processed by a whole slide image processing system 610.

Whole slide image generation system 620 can transmit an image produced by image scanner 624 back to user device 630. User device 630 then communicates with the whole slide image processing system 610 to initiate automated processing of the image. In some instances, whole slide image generation system 620 provides an image produced by image scanner 624 to the whole slide image processing system 610 directly, e.g. at the direction of the user of a user device 630. Although not illustrated, other intermediary devices (e.g., data stores of a server connected to the whole slide image generation system 620 or whole slide image processing system 610) can also be used. Additionally, for the sake of simplicity only one whole slide image processing system 610, image generating system 620, and user device 630 is illustrated in the network 600. This disclosure anticipates the use of one or more of each type of system and component thereof without necessarily deviating from the teachings of this disclosure.

The network 600 and associated systems shown in FIG. 6 can be used in a variety of contexts where scanning and evaluation of digital pathology images, such as whole slide images, are an essential component of the work. As an example, the network 600 can be associated with a clinical environment, where a user is evaluating the sample for possible diagnostic purposes. The user can review the image using the user device 630 prior to providing the image to the whole slide image processing system 610. The user can provide additional information to the whole slide image processing system 610 that can be used to guide or direct the analysis of the image by the whole slide image processing system 610. For example, the user can provide a prospective diagnosis or preliminary assessment of features within the scan. The user can also provide additional context, such as the type of tissue being reviewed. As another example, the network 600 can be associated with a laboratory environment were tissues are being examined, for example, to determine the efficacy or potential side effects of a drug. In this context, it can be commonplace for multiple types of tissues to be submitted for review to determine the effects on the whole body of said drug. This can present a particular challenge to human scan reviewers, who may need to determine the various contexts of the images, which can be highly dependent on the type of tissue being imaged. These contexts can optionally be provided to the whole slide image processing system 610.

Whole slide image processing system 610 can process digital pathology images, including whole slide images, to classify the digital pathology images and generate annotations for the digital pathology images and related output. A tile generating module 611 can define a set of tiles for each digital pathology image. To define the set of tiles, the tile generating module 611 can segment the digital pathology image into the set of tiles. As embodied herein, the tiles can be non-overlapping (e.g., each tile includes pixels of the image not included in any other tile) or overlapping (e.g., each tile includes some portion of pixels of the image that are included in at least one other tile). Features such as whether or not tiles overlap, in addition to the size of each tile and the stride of the window (e.g., the image distance or pixels between a tile and a subsequent tile) can increase or decrease the data set for analysis, with more tiles (e.g., through overlapping or smaller tiles) increasing the potential resolution of eventual output and visualizations. In some instances, tile generating module 611 defines a set of tiles for an image where each tile is of a predefined size and/or an offset between tiles is predefined. Furthermore, the tile generating module 611 can create multiple sets of tiles of varying size, overlap, step size, etc., for each image. In some embodiments, the digital pathology image itself can contain tile overlap, which may result from the imaging technique. Even segmentation without tile overlapping can be a preferable solution to balance tile processing requirements and avoid influencing the embedding generation and weighting value generation discussed herein. A tile size or tile offset can be determined, for example, by calculating one or more performance metrics (e.g., precision, recall, accuracy, and/or error) for each size/offset and by selecting a tile size and/or offset associated with one or more performance metrics above a predetermined threshold and/or associated with one or more optimal (e.g., high precision, highest recall, highest accuracy, and/or lowest error) performance metric(s).

The tile generating module 611 may further define a tile size depending on the type of abnormality being detected. For example, the tile generating module 611 can be configured with awareness of the type(s) of tissue abnormalities that the whole slide image processing system 610 will be searching for and can customize the tile size according to the tissue abnormalities to optimize detection. For example, the image generating module 611 can determine that, when the tissue abnormalities include searching for inflammation or necrosis in lung tissue, the tile size should be reduced to increase the scanning rate, while when the tissue abnormalities include abnormalities with Kupffer cells in liver tissues, the tile size should be increased to increase the opportunities for the whole slide image processing system 610 to analyze the Kupffer cells holistically. In some instances, tile generating module 611 defines a set of tiles where a number of tiles in the set, size of the tiles of the set, resolution of the tiles for the set, or other related properties, for each image is defined and held constant for each of one or more images.

As embodied herein, the tile generating module 611 can further define the set of tiles for each digital pathology image along one or more color channels or color combinations. As an example, digital pathology images received by whole slide image processing system 610 can include large-format multi-color channel images having pixel color values for each pixel of the image specified for one of several color channels. Example color specifications or color spaces that can be used include the RGB, CMYK, HSL, HSV, or HSB color specifications. The set of tiles can be defined based on segmenting the color channels and/or generating a brightness map or greyscale equivalent of each tile. For example, for each segment of an image, the tile generating module 611 can provide a red tile, blue tile, green tile, and/or brightness tile, or the equivalent for the color specification used. As explained herein, segmenting the digital pathology images based on segments of the image and/or color values of the segments can improve the accuracy and recognition rates of the networks used to generating embeddings for the tiles and image and to produce classifications of the image. Additionally, the whole slide image processing system 610, e.g., using tile generating module 611, can convert between color specifications and/or prepare copies of the tiles using multiple color specifications. Color specification conversions can be selected based on a desired type of image augmentation (e.g., accentuating or boosting particular color channels, saturation levels, brightness levels, etc.). Color specification conversions can also be selected to improve compatibility between whole slide image generation systems 620 and the whole slide image processing system 610. For example, a particular image scanning component can provide output in the HSL color specification and the models used in the whole slide image processing system 610, as described herein, can be trained using RGB images. Converting the tiles to the compatible color specification can ensure the tiles can still be analyzed. Additionally, the whole slide image processing system can up-sample or down-sample images that are provided in particular color depth (e.g., 8-bit, 66-bit, etc.) to be usable by the whole slide image processing system. Furthermore, the whole slide image processing system 610 can cause tiles to be converted according to the type of image that has been captured (e.g., fluorescent images may include greater detail on color intensity or a wider range of colors).

As described herein, a tile embedding module 612 can generate an embedding for each tile in a corresponding feature embedding space. The embedding can be represented by the whole slide image processing system 610 as a feature vector for the tile. The tile embedding module 612 can use a neural network (e.g., a convolutional neural network) to generate a feature vector that represents each tile of the image. In particular embodiments, the tile embedding neural network can be based on the ResNet image network trained on a dataset based on natural (e.g., non-medical) images, such as the ImageNet dataset. By using a non-specialized tile embedding network, the tile embedding module 612 can leverage known advances in efficiently processing images to generating embeddings. Furthermore, using a natural image dataset allows the embedding neural network to learn to discern differences between tile segments on a holistic level.

In other embodiments, the tile embedding network used by the tile embedding module 612 can be an embedding network customized to handle large numbers of tiles of large format images, such as digital pathology whole slide images. Additionally, the tile embedding network used by the tile embedding module 612 can be trained using a custom dataset. For example, the tile embedding network can be trained using a variety of samples of whole slide images or even trained using samples relevant to the subject matter for which the embedding network will be generating embeddings (e.g., scans of particular tissue types). Training the tile embedding network using specialized or customized sets of images can allow the tile embedding network to identify finer differences between tiles which can result in more detailed and accurate distances between tiles in the feature embedding space at the cost of additional time to acquire the images and the computational and economic cost of training multiple tile generating networks for use by the tile embedding module 612. The tile embedding module 612 can select from a library of tile embedding networks based on the type of images being processed by the whole slide image processing system 610.

As described herein, tile embeddings can be generated from a deep learning neural network using visual features of the tiles. Tile embeddings can be further generated from contextual information associated with the tiles or from the content shown in the tile. For example, a tile embedding can include one or more features that indicate and/or correspond to a size of depicted objects (e.g., sizes of depicted cells or aberrations) and/or density of depicted objects (e.g., a density of depicted cells or aberrations). Size and density can be measured absolutely (e.g., width expressed in pixels or converted from pixels to nanometers) or relative to other tiles from the same digital pathology image, from a class of digital pathology images (e.g., produced using similar techniques or by a single whole slide image generation system or scanner), or from a related family of digital pathology images. Furthermore, tiles can be classified prior to the tile embedding module 612 generating embeddings for the tiles such that the tile embedding module 612 considers the classification when preparing the embeddings.

For consistency, the tile embedding module 612 produces embeddings of a predefined size (e.g., vectors of 512 elements, vectors of 2048 bytes, etc.). The tile embedding module 612 can produce embeddings of various and arbitrary sizes. The time embedding module 612 can adjust the sizes of the embeddings based on user direction or can be selected, for example, to optimize computation efficiency, accuracy, or other parameters. In particular embodiments, the embedding size can be based on the limitations or specifications of the deep learning neural network that generated the embeddings. Larger embedding sizes can be used to increase the amount of information captured in the embedding and improve the quality and accuracy of results, while smaller embedding sizes can be used to improve computational efficiency.

A whole slide image access module 613 can manage requests to access whole slide images from other modules of the whole slide image processing system 610 and the user device 630. For example, the whole slide image access module 613 receive requests to identify a whole slide image based on a particular tile, an identifier for the tile, or an identifier for the whole slide image. The whole slide image access module 613 can perform tasks of confirming that the whole slide image is available to the user requesting, identifying the appropriate databases from which to retrieve the requested whole slide image, and retrieving any additional metadata that may be of interest to the requesting user or module. Additionally, the whole slide image access module 613 can handle efficiently streaming the appropriate data to the requesting device. As described herein, whole slide images may be provided to user devices in chunks, based on the likelihood that a user will wish to see the portion of the whole slide image. The whole slide image access module 613 can determine which regions of the whole slide image to provide and determine how best to provide them. Furthermore, the whole slide image access module 613 can be empowered within the whole slide image processing system 610 to ensure that no individual component locks up or otherwise misuses a database or whole slide image to the detriment of other components or users.

An output generating module 614 of the whole slide image processing system 610 can generate output corresponding to result tile and result whole slide image datasets based on user request. As described herein, the output can include a variety of visualizations, interactive graphics, and reports based upon the type of request and the type of data that is available. In many embodiments, the output will be provided to the user device 630 for display, but in certain embodiments the output can be accessed directly from the whole slide image processing system 610. The output will be based on existence of and access to the appropriate data, so the output generating module will be empowered to access necessarily metadata and anonymized patient information as needed. As with the other modules of the whole slide image processing system 610, the output generating module 614 can be updated and improved in a modular fashion, so that new output features can be provided to users without requiring significant downtime.

The general techniques described herein can be integrated into a variety of tools and use cases. For example, as described, a user (e.g., pathology or clinician) can access a user device 630 that is in communication with the whole slide image processing system 610 and provide a query image for analysis. The whole slide image processing system 610, or the connection to the whole slide image processing system can be provided as a standalone software tool or package that searches for corresponding matches, identifies similar features, and generates appropriate output for the user upon request. As a standalone tool or plug-in that can be purchased or licensed on a streamlined basis, the tool can be used to augment the capabilities of a research or clinical lab. Additionally, the tool can be integrated into the services made available to the customer of whole slide image generation systems. For example, the tool can be provided as a unified workflow, where a user who conducts or requests a whole slide image to be created automatically receives a report of noteworthy features within the image and/or similar whole slide images that have been previously indexed. Therefore, in addition to improving whole slide image analysis, the techniques can be integrated into existing systems to provide additional features not previously considered or possible.

Moreover, the whole slide image processing system 610 can be trained and customized for use in particular settings. For example, the whole slide image processing system 610 can be specifically trained for use in providing insights relating to specific types of tissue (e.g., lung, heart, blood, liver, etc.). As another example, the whole slide image processing system 610 can be trained to assist with safety assessment, for example in determining levels or degrees of toxicity associated with drugs or other potential therapeutic treatments. Once trained for use in a specific subject matter or use case, the whole slide image processing system 610 is not necessarily limited to that use case. Training may be performed in a particular context, e.g., toxicity assessment, due to a relatively larger set of at least partially labeled or annotated images.

Figure 7:
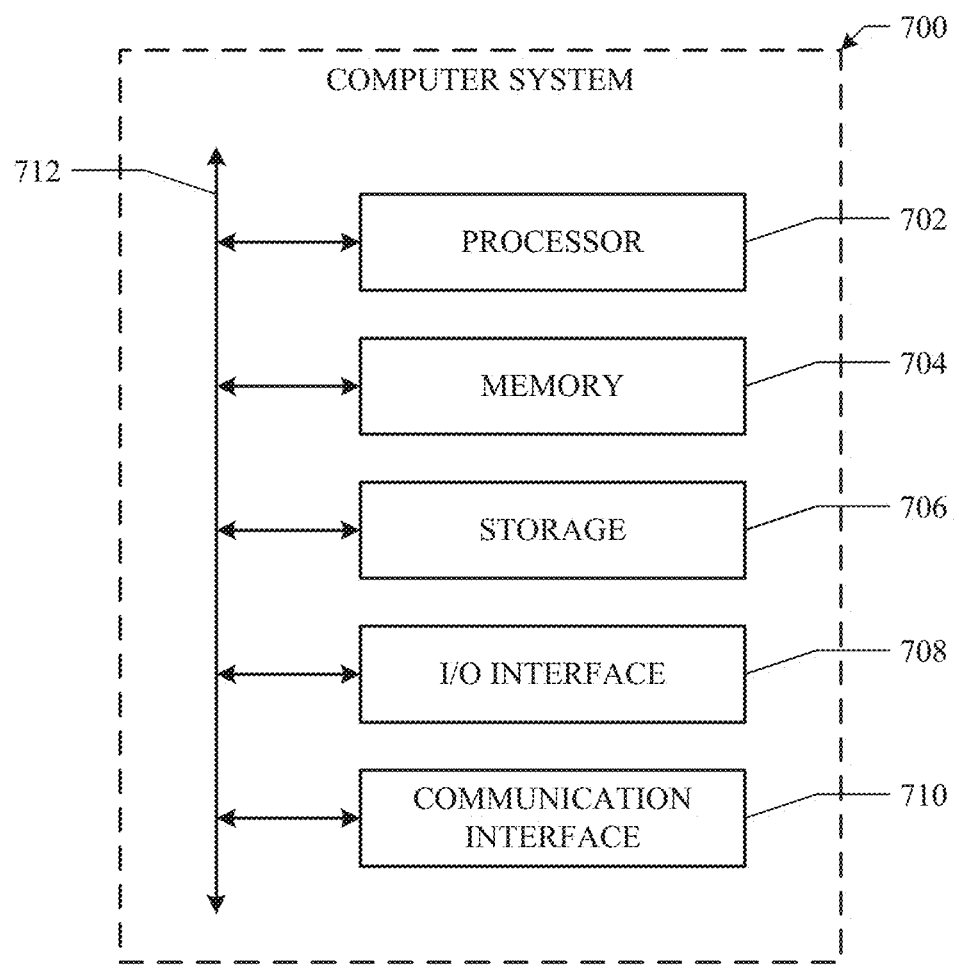
FIG. 7 illustrates an example computer system.

FIG. 7 illustrates an example computer system. In particular embodiments, one or more computer systems 700 perform one or more steps of one or more methods described or illustrated herein. In particular embodiments, one or more computer systems 700 provide functionality described or illustrated herein. In particular embodiments, software running on one or more computer systems 700 performs one or more steps of one or more methods described or illustrated herein or provides functionality described or illustrated herein. Particular embodiments include one or more portions of one or more computer systems 700. Herein, reference to a computer system may encompass a computing device, and vice versa, where appropriate. Moreover, reference to a computer system may encompass one or more computer systems, where appropriate.

This disclosure contemplates any suitable number of computer systems 700. This disclosure contemplates computer system 700 taking any suitable physical form. As example and not by way of limitation, computer system 700 may be an embedded computer system, a system-on-chip (SOC), a single-board computer system (SBC) (such as, for example, a computer-on-module (COM) or system-on-module (SOM)), a desktop computer system, a laptop or notebook computer system, an interactive kiosk, a mainframe, a mesh of computer systems, a mobile telephone, a personal digital assistant (PDA), a server, a tablet computer system, or a combination of two or more of these. Where appropriate, computer system 700 may include one or more computer systems 700; be unitary or distributed; span multiple locations; span multiple machines; span multiple data centers; or reside in a cloud, which may include one or more cloud components in one or more networks. Where appropriate, one or more computer systems 700 may perform without substantial spatial or temporal limitation one or more steps of one or more methods described or illustrated herein. As an example and not by way of limitation, one or more computer systems 700 may perform in real time or in batch mode one or more steps of one or more methods described or illustrated herein. One or more computer systems 700 may perform at different times or at different locations one or more steps of one or more methods described or illustrated herein, where appropriate.

In particular embodiments, computer system 700 includes a processor 702, memory 704, storage 706, an input/output (I/O) interface 708, a communication interface 710, and a bus 712. Although this disclosure describes and illustrates a particular computer system having a particular number of particular components in a particular arrangement, this disclosure contemplates any suitable computer system having any suitable number of any suitable components in any suitable arrangement.

In particular embodiments, processor 702 includes hardware for executing instructions, such as those making up a computer program. As an example and not by way of limitation, to execute instructions, processor 702 may retrieve (or fetch) the instructions from an internal register, an internal cache, memory 704, or storage 706; decode and execute them; and then write one or more results to an internal register, an internal cache, memory 704, or storage 706. In particular embodiments, processor 702 may include one or more internal caches for data, instructions, or addresses. This disclosure contemplates processor 702 including any suitable number of any suitable internal caches, where appropriate. As an example and not by way of limitation, processor 702 may include one or more instruction caches, one or more data caches, and one or more translation lookaside buffers (TLBs). Instructions in the instruction caches may be copies of instructions in memory 704 or storage 706, and the instruction caches may speed up retrieval of those instructions by processor 702. Data in the data caches may be copies of data in memory 704 or storage 706 for instructions executing at processor 702 to operate on; the results of previous instructions executed at processor 702 for access by subsequent instructions executing at processor 702 or for writing to memory 704 or storage 706; or other suitable data. The data caches may speed up read or write operations by processor 702. The TLBs may speed up virtual-address translation for processor 702. In particular embodiments, processor 702 may include one or more internal registers for data, instructions, or addresses. This disclosure contemplates processor 702 including any suitable number of any suitable internal registers, where appropriate. Where appropriate, processor 702 may include one or more arithmetic logic units (ALUs); be a multi-core processor; or include one or more processors 702. Although this disclosure describes and illustrates a particular processor, this disclosure contemplates any suitable processor.

In particular embodiments, memory 704 includes main memory for storing instructions for processor 702 to execute or data for processor 702 to operate on. As an example and not by way of limitation, computer system 700 may load instructions from storage 706 or another source (such as, for example, another computer system 700) to memory 704. Processor 702 may then load the instructions from memory 704 to an internal register or internal cache. To execute the instructions, processor 702 may retrieve the instructions from the internal register or internal cache and decode them. During or after execution of the instructions, processor 702 may write one or more results (which may be intermediate or final results) to the internal register or internal cache. Processor 702 may then write one or more of those results to memory 704. In particular embodiments, processor 702 executes only instructions in one or more internal registers or internal caches or in memory 704 (as opposed to storage 706 or elsewhere) and operates only on data in one or more internal registers or internal caches or in memory 704 (as opposed to storage 706 or elsewhere). One or more memory buses (which may each include an address bus and a data bus) may couple processor 702 to memory 704. Bus 712 may include one or more memory buses, as described below. In particular embodiments, one or more memory management units (MMUs) reside between processor 702 and memory 704 and facilitate accesses to memory 704 requested by processor 702. In particular embodiments, memory 704 includes random access memory (RAM). This RAM may be volatile memory, where appropriate. Where appropriate, this RAM may be dynamic RAM (DRAM) or static RAM (SRAM). Moreover, where appropriate, this RAM may be single-ported or multi-ported RAM. This disclosure contemplates any suitable RAM. Memory 704 may include one or more memories 704, where appropriate. Although this disclosure describes and illustrates particular memory, this disclosure contemplates any suitable memory.

In particular embodiments, storage 706 includes mass storage for data or instructions. As an example and not by way of limitation, storage 706 may include a hard disk drive (HDD), a floppy disk drive, flash memory, an optical disc, a magneto-optical disc, magnetic tape, or a Universal Serial Bus (USB) drive or a combination of two or more of these. Storage 706 may include removable or non-removable (or fixed) media, where appropriate. Storage 706 may be internal or external to computer system 700, where appropriate. In particular embodiments, storage 706 is non-volatile, solid-state memory. In particular embodiments, storage 706 includes read-only memory (ROM). Where appropriate, this ROM may be mask-programmed ROM, programmable ROM (PROM), erasable PROM (EPROM), electrically erasable PROM (EEPROM), electrically alterable ROM (EAROM), or flash memory or a combination of two or more of these. This disclosure contemplates mass storage 706 taking any suitable physical form. Storage 706 may include one or more storage control units facilitating communication between processor 702 and storage 706, where appropriate. Where appropriate, storage 706 may include one or more storages 706. Although this disclosure describes and illustrates particular storage, this disclosure contemplates any suitable storage.

In particular embodiments, I/O interface 708 includes hardware, software, or both, providing one or more interfaces for communication between computer system 700 and one or more I/O devices. Computer system 700 may include or be communicably connected to one or more of these I/O (input/output) devices, where appropriate. One or more of these I/O devices may enable communication between a person and computer system 700. An input device coupled to the I/O interface 708 may include devices for converting different forms of volitional user input into digital signals that can be processed by computer system 700, for example and not by way of limitation, a keyboard, a keypad, microphone (e.g., to provide audio input), a camera (e.g., to provide gesture input or facial/body expression input), a mouse or trackball, stylus, touch screen, digital glove, hand-held 3D controller, head-mounted controller, optical motion-sensing systems (comprising infrared light projectors and detectors and/or cameras), non-optical (e.g., inertial, mechanical, magnetic, or stretch sensor-based) motion-capture systems, another suitable input device, or a combination of two or more of these. An input device may include one or more sensors for capturing different types of information. As an example and not by way of limitation, a sensor may include a still image camera, video camera, image scanner, 3D scanning system (e.g., based on computed tomography, microtomography, magnetic resonance imaging, modulated light, laser triangulation, laser pulse, structured light, light detection and ranging (LiDAR)), infrared camera, accelerometer, gyroscope, magnetometer, global positioning satellite (GPS) signal sensor, vibration sensor (e.g., piezoelectric accelerometer), pressure sensor, meteorological sensors (e.g., for measuring solar radiation, air temperature, barometric pressure, precipitation, relative humidity, wind direction, and wind speed), chemical sensors, electromagnetic radiation sensors, nuclear radiation sensors, another suitable sensor, or a combination thereof. An output device may include devices designed to receive digital signals from computer system 700 and convert them to some output format, for example and not by way of limitation, a paper or other 2D-media printer, 3D printer, speaker, headphones, projector, monitor, heads-up display, vehicle, drone, robot, another suitable output device, or a combination thereof. This disclosure contemplates any suitable I/O device and any suitable I/O interface 708 for them. Where appropriate, I/O interface 708 may include one or more device or software drivers enabling processor 702 to drive one or more of these I/O devices. I/O interface 708 may include one or more I/O interfaces 708, where appropriate. Although this disclosure describes and illustrates a particular I/O interface, this disclosure contemplates any suitable I/O interface.

In particular embodiments, communication interface 710 includes hardware, software, or both providing one or more interfaces for communication (such as, for example, packet-based communication) between computer system 700 and one or more other computer systems 700 or one or more networks. As an example and not by way of limitation, communication interface 710 may include a network interface controller (NIC) or network adapter for communicating with an Ethernet or other wire-based network or a wireless NIC (WNIC) or wireless adapter for communicating with a wireless network, such as a WI-FI network. This disclosure contemplates any suitable network and any suitable communication interface 710 for it. As an example and not by way of limitation, computer system 700 may communicate with an ad hoc network, a personal area network (PAN), a local area network (LAN), a wide area network (WAN), a metropolitan area network (MAN), or one or more portions of the Internet or a combination of two or more of these. One or more portions of one or more of these networks may be wired or wireless. As an example, computer system 700 may communicate with a wireless PAN (WPAN) (such as, for example, a BLUETOOTH WPAN), a WI-FI network, a WI-MAX network, a cellular telephone network (such as, for example, a Global System for Mobile Communications (GSM) network), or other suitable wireless network or a combination of two or more of these. Computer system 700 may include any suitable communication interface 710 for any of these networks, where appropriate. Communication interface 710 may include one or more communication interfaces 710, where appropriate. Although this disclosure describes and illustrates a particular communication interface, this disclosure contemplates any suitable communication interface.

In particular embodiments, bus 712 includes hardware, software, or both coupling components of computer system 700 to each other. As an example and not by way of limitation, bus 712 may include an Accelerated Graphics Port (AGP) or other graphics bus, an Enhanced Industry Standard Architecture (EISA) bus, a front-side bus (FSB), a HYPERTRANSPORT (HT) interconnect, an Industry Standard Architecture (ISA) bus, an INFINIBAND interconnect, a low-pin-count (LPC) bus, a memory bus, a Micro Channel Architecture (MCA) bus, a Peripheral Component Interconnect (PCI) bus, a PCI-Express (PCIe) bus, a serial advanced technology attachment (SATA) bus, a Video Electronics Standards Association local (VLB) bus, or another suitable bus or a combination of two or more of these. Bus 712 may include one or more buses 712, where appropriate. Although this disclosure describes and illustrates a particular bus, this disclosure contemplates any suitable bus or interconnect.

Herein, "or" is inclusive and not exclusive, unless expressly indicated otherwise or indicated otherwise by context. Therefore, herein, "A or B" means "A, B, or both," unless expressly indicated otherwise or indicated otherwise by context. Moreover, "and" is both joint and several, unless expressly indicated otherwise or indicated otherwise by context. Therefore, herein, "A and B" means "A and B, jointly or severally," unless expressly indicated otherwise or indicated otherwise by context.

The scope of this disclosure encompasses all changes, substitutions, variations, alterations, and modifications to the example embodiments described or illustrated herein that a person having ordinary skill in the art would comprehend. The scope of this disclosure is not limited to the example embodiments described or illustrated herein. Moreover, although this disclosure describes and illustrates respective embodiments herein as including particular components, elements, feature, functions, operations, or steps, any of these embodiments may include any combination or permutation of any of the components, elements, features, functions, operations, or steps described or illustrated anywhere herein that a person having ordinary skill in the art would comprehend. Furthermore, reference in the appended claims to an apparatus or system or a component of an apparatus or system being adapted to, arranged to, capable of, configured to, enabled to, operable to, or operative to perform a particular function encompasses that apparatus, system, component, whether or not it or that particular function is activated, turned on, or unlocked, as long as that apparatus, system, or component is so adapted, arranged, capable, configured, enabled, operable, or operative. Additionally, although this disclosure describes or illustrates particular embodiments as providing particular advantages, particular embodiments may provide none, some, or all of these advantages.

The invention claimed is:

1. A method for anomaly detection, comprising:
   receiving, by an image processing system, an image of a tissue sample;
   generating, by the image processing system, a set of tiles of the image of the tissue sample;
   inputting, by the image processing system, the set of tiles into an anomaly detection model, the anomaly detection model comprising:
   a generator model comprising functional skip-connections; and
   a Markovian discriminator model;

wherein the anomaly detection model was trained to isolate a feature space of normal tissue samples;

computing, by the image processing system, anomaly scores for the set of tiles; and generating, by the image processing system and based on the anomaly scores for the set of tiles, an assessment for the image of the tissue sample, wherein the assessment identifies the image of the tissue sample as including abnormal tissue.

2. The method of claim 1, wherein generating the set of tiles further comprises:

extracting tiles of interest, wherein the set of tiles comprises only tiles of interest.

3. The method of claim 1, wherein generating the set of tiles comprises:

segmenting the image of the tissue sample into tiles at a plurality of scales of the image, each of the scales representing multiple channels of input.

4. The method of claim 3, wherein generating the assessment for the image of the tissue sample comprises:

concatenating the plurality of scales of the image to generate a hyper-dimensional image containing multiple levels of information.

5. The method of claim 4, wherein the concatenated plurality of scales of the image are symmetric about a central pixel along a channel axis.

6. The method of claim 5, further comprising de-blurring the heatmap image.

7. The method of claim 1, wherein generating the assessment for the image of the tissue sample comprises:

mapping each unique score of the anomaly scores to a distinct color; and generating, based on the mapping and the anomaly scores for tiles in the set of tiles, a heatmap image of the image of the tissue sample, wherein each of the tiles in the heatmap image is depicted in the distinct color mapped to the anomaly score for the tile.

8. The method of claim 1, wherein the computing an anomaly score for the tiles comprises computing an anomaly score for each of a plurality of overlapping patches of the tiles.

9. The method of claim 1, further comprising normalizing the anomaly scores to fall within a range from 0 to 1.

10. The method of claim 1, wherein the anomaly score for each of the tiles is computed as a function of a loss of the generator model and a loss of the Markovian discriminator model, wherein the loss of the generator model is determined as between the tile and a corresponding reconstruction of the tile, and wherein the loss of the Markovian discriminator model is determined as between an output of the Markovian discriminator model for the tile and an output of the Markovian discriminator model for the corresponding reconstruction of the tile.

11. The method of claim 10, wherein training the anomaly detection model is based on a combined loss comprising an adversarial loss, a reconstruction loss, and a latent loss.

12. The method of claim 10, wherein training the anomaly detection model is based on a reconstruction loss comprising a perceptual loss based on a structural similarity metric.

13. The method of claim 1, further comprising:

training the anomaly detection model to isolate a feature space of normal tissue samples by using a one-class data set comprising images of normal tissue.

14. The method of claim 1, wherein the functional skip-connections are regularized by randomly dropping at least one node from the generator network for at least one of the training tiles.

15. One or more computer-readable non-transitory storage media embodying software comprising instructions operable when executed to:

receive, by an image processing system, an image of a tissue sample;

generate, by the image processing system, a set of tiles of the image of the tissue sample;

input, by the image processing system, the set of tiles into an anomaly detection model, the anomaly detection model comprising:

a generator model comprising functional skip-connections; and a Markovian discriminator model;

wherein the anomaly detection model was trained to isolate a feature space of normal tissue samples;

compute, by the image processing system, anomaly scores for the set of tiles; and generate, by the image processing system and based on the anomaly scores for the set of tiles, an assessment for the image of the tissue sample, wherein the assessment identifies the image of the tissue sample as including abnormal tissue.

16. The computer-readable non-transitory storage media of claim 15, wherein instructions operable when executed to generate the assessment for the image of the tissue sample comprises instructions operable when executed to:

map each unique score of the anomaly scores to a distinct color; and generate, based on the mapping and the anomaly scores for tiles in the set of tiles, a heatmap image of the image of the tissue sample, wherein each of the tiles in the heatmap image is depicted in the distinct color mapped to the anomaly score for the tile.

17. The computer-readable non-transitory storage media of claim 15, the software further comprising instructions operable when executed to:

train the anomaly detection model to isolate a feature space of normal tissue samples by using a one-class data set comprising images of normal tissue.

18. A image processing system comprising one or more processors and a memory coupled to the processors comprising instructions executable by the processors, the processors being operable when executing the instructions to:

receive an image of a tissue sample;

generate a set of tiles of the image of the tissue sample;

input the set of tiles into an anomaly detection model, the anomaly detection model comprising:

a generator model comprising functional skip-connections; and a Markovian discriminator model;

wherein the anomaly detection model was trained to isolate a feature space of normal tissue samples;

compute anomaly scores for the set of tiles; and generate, based on the anomaly scores for the set of tiles, an assessment for the image of the tissue sample, wherein the assessment identifies the image of the tissue sample as including abnormal tissue.

19. The image processing system of claim 18, wherein the processors being operable when executing the instructions to generate the assessment for the image of the tissue sample comprises the processors being operable when executing the instructions to:

map each unique score of the anomaly scores to a distinct color; and generate, based on the mapping and the anomaly scores for tiles in the set of tiles, a heatmap image of the image of the tissue sample, wherein each of the tiles in the heatmap image is depicted in the distinct color mapped to the anomaly score for the tile.

20. The image processing system of claim 18, the processors being further operable when executing the instructions to:
   train the anomaly detection model to isolate a feature space of normal tissue samples by using a one-class data set comprising images of normal tissue.

\* \* \* \* \*

UNITED STATES PATENT AND TRADEMARK OFFICE
CERTIFICATE OF CORRECTION

PATENT NO. : 12,283,365 B2  
APPLICATION NO. : 17/695786  
DATED : April 22, 2025  
INVENTOR(S) : Fang-Yao Hu Page 1 of 1

It is certified that error appears in the above-identified patent and that said Letters Patent is hereby corrected as shown below:

In the Claims

At Column 23, Claim number 6, Line numbers 27-28, delete "The method of claim 5, further comprising de-blurring the heatmap image." and insert --The method of claim 1, wherein generating the assessment for the image of the tissue sample comprises: mapping each unique score of the anomaly scores to a distinct color; and generating, based on the mapping and the anomaly scores for tiles in the set of tiles, a heatmap image of the image of the tissue sample, wherein each of the tiles in the heatmap image is depicted in the distinct color mapped to the anomaly score for the tile.--

At Column 23, Claim number 7, Line numbers 29-37, please delete "The method of claim 1, wherein generating the assessment for the image of the tissue sample comprises: mapping each unique score of the anomaly scores to a distinct color; and generating, based on the mapping and the anomaly scores for tiles in the set of tiles, a heatmap image of the image of the tissue sample, wherein each of the tiles in the heatmap image is depicted in the distinct color mapped to the anomaly score for the tile." and insert --The method of claim 6, further comprising de-blurring the heatmap image.--

Signed and Sealed this  
Twentieth Day of May, 2025

Coke Morgan Stewart  
*Acting Director of the United States Patent and Trademark Office*